US012036136B2

United States Patent
Allen

(10) Patent No.: US 12,036,136 B2
(45) Date of Patent: *Jul. 16, 2024

(54) PROSTHETIC SOCKET SYSTEMS AND METHODS

(71) Applicant: Personal Performance Medical Corporation, Midvale, UT (US)

(72) Inventor: Scott E. Allen, South Jordan, UT (US)

(73) Assignee: Personal Performance Medical Corporation, Midvale, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 18/462,857

(22) Filed: Sep. 7, 2023

(65) Prior Publication Data

US 2023/0414382 A1    Dec. 28, 2023

Related U.S. Application Data

(63) Continuation of application No. 17/466,414, filed on Sep. 3, 2021, now Pat. No. 11,752,017.

(60) Provisional application No. 63/074,248, filed on Sep. 3, 2020.

(51) Int. Cl.
    *A61F 2/78*    (2006.01)
    *A61F 2/50*    (2006.01)
    *A61F 2/70*    (2006.01)
    *A61F 2/80*    (2006.01)

(52) U.S. Cl.
    CPC .......... *A61F 2/7843* (2013.01); *A61F 2/5046* (2013.01); *A61F 2/70* (2013.01); *A61F 2/80* (2013.01); *A61F 2002/5032* (2013.01); *A61F 2002/5083* (2013.01)

(58) Field of Classification Search
    CPC ........ A61F 2/7843; A61F 2/5046; A61F 2/70; A61F 2/80; A61F 2002/5032; A61F 2002/5083
    See application file for complete search history.

(56) References Cited

U.S. PATENT DOCUMENTS

| | | | |
|---|---|---|---|
| 5,156,629 A | 10/1992 | Shane | |
| 6,361,569 B1 | 3/2002 | Slemker et al. | |
| 7,655,049 B2 | 2/2010 | Phillips | |
| 10,010,433 B2 | 7/2018 | Layman et al. | |
| 11,752,017 B2 * | 9/2023 | Allen ........................ | A61F 2/70 623/24 |
| 2003/0181990 A1 | 9/2003 | Phillips | |

(Continued)

OTHER PUBLICATIONS

Carpinteiro, "Laser scanning system for 3D modeling of prostheses inner surface," Jun. 2014, pp. 31-40.

(Continued)

*Primary Examiner* — Jerrah Edwards
*Assistant Examiner* — Maximilian Tobias Spencer
(74) *Attorney, Agent, or Firm* — PCFB, LLC; Justin K Flanagan

(57) ABSTRACT

Systems and methods are described herein for a prosthetic device that includes a rigid outer shell socket with an inner surface contour. A prosthetic insert socket is manufactured via a manufacturing process, such as three-dimensional printing, to have an outer contour that corresponds to the inner surface contour of the premade outer shell socket. The prosthetic insert socket is manufactured to have an inner contour that corresponds to a residual limb surface contour of a patient.

20 Claims, 21 Drawing Sheets

(56) References Cited

U.S. PATENT DOCUMENTS

| | | |
|---|---|---|
| 2015/0366680 A1 | 12/2015 | Accinni et al. |
| 2017/0209290 A1 | 7/2017 | Birgisdottir et al. |
| 2018/0368996 A1 | 12/2018 | Van Vliet et al. |
| 2019/0117420 A1 | 4/2019 | Storup |
| 2020/0390568 A1 | 12/2020 | Joseph |
| 2021/0145608 A1 | 5/2021 | Herr et al. |
| 2021/0386565 A1 | 12/2021 | Joseph et al. |

OTHER PUBLICATIONS

U.S. Appl. No. 17/466,414, Non-Final Office Action mailed Oct. 4, 2022, 21 pp.
U.S. Appl. No. 17/466,414, Final Office Action mailed May 2, 2023, 23 pp.
Miller, et al. "A novel, low-cost transradial socket fabrication method using mass-producible component and expanding rigid foam," Prosthetics and Orthotics International (2020): 0309364620950850. (Year: 2020).

* cited by examiner

PROSTHETIC SOCKET SYSTEMS AND METHODS

RELATED APPLICATIONS

This application is a continuation of U.S. patent application Ser. No. 17/466,414 titled "Prosthetic Socket Systems and Methods" filed on Sep. 3, 2021, which application claims priority to and benefits under 35 U.S.C. § 119 to U.S. Provisional Patent Application No. 63/074,248 titled "Prosthetic Socket Systems and Methods" filed on Sep. 3, 2020, both of which are hereby incorporated by reference in their entireties.

TECHNICAL FIELD

This application generally relates to prosthetic systems. More specifically, this application relates to customized, customizable, and adjustable prosthetic sockets.

BRIEF DESCRIPTION OF THE DRAWINGS

The written disclosure herein describes illustrative embodiments that are nonlimiting and non-exhaustive. This disclosure references certain of such illustrative embodiments depicted in the figures described below.

DETAILED DESCRIPTION

Figure 1A:
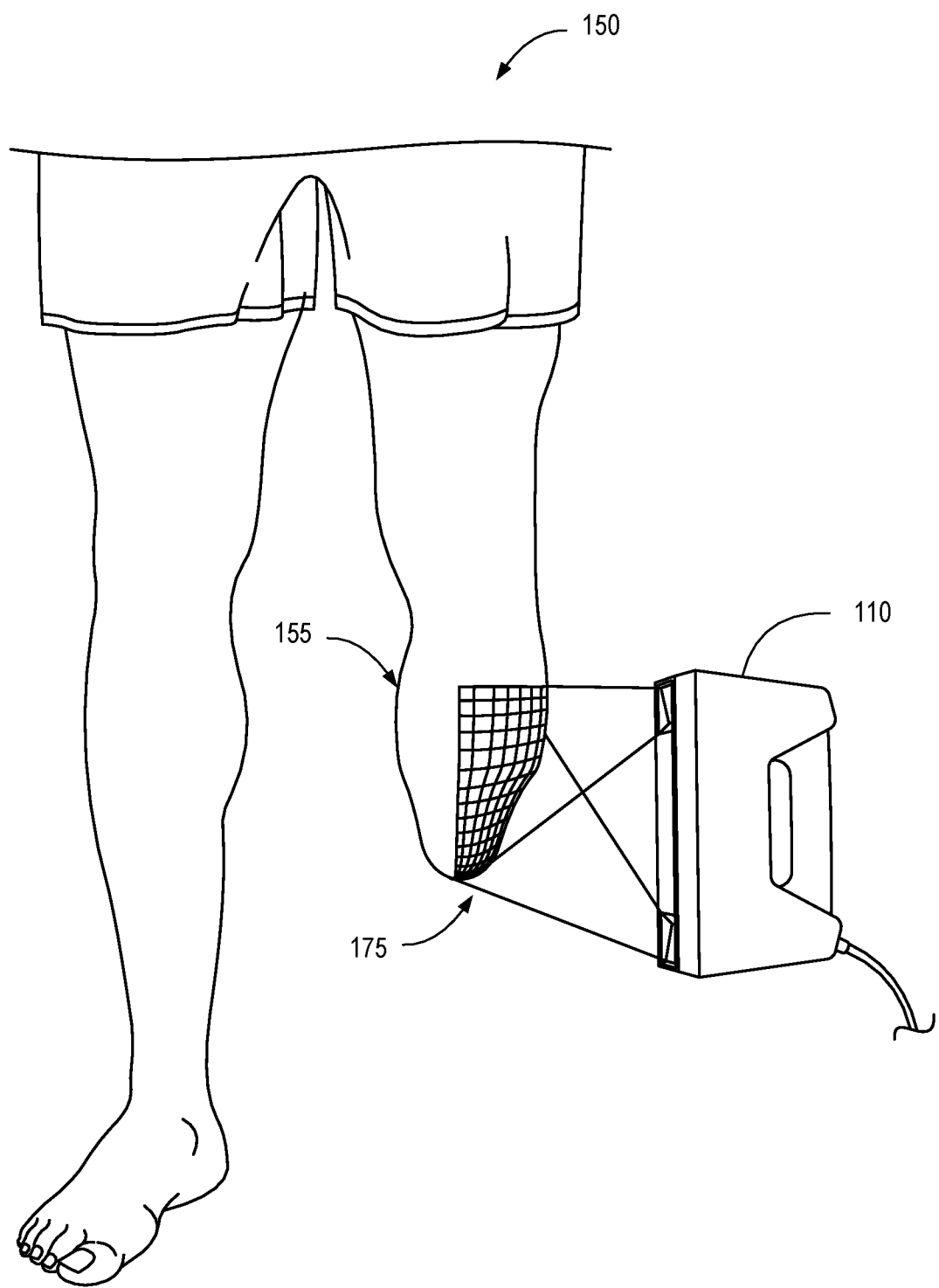
FIG. 1A illustrates an example of a three-dimensional scanner to determine a three-dimensional residual limb surface contour, according to one embodiment.

The disclosure describes systems and methods relating to prosthetic devices. In various examples, a contour of a residual limb is determined for fitting a customized multi-piece prosthetic device thereto. For example, a three-dimensional scanner may be used to scan a residual limb to determine a residual limb surface contour. In other instances, a residual limb surface contour may be manually measured or electronically imaged. In still other embodiments, a moldable or pliable material may be cast or molded to the residual limb. The casting may be used to develop a positive mold of the residual limb that can be measured (electronically or manually) and/or used to shape an inner contour of a customized prosthetic insert socket.

A customized prosthetic insert socket may be formed to have an inner contour that conforms to the residual limb surface contour. The customized prosthetic insert socket may be customized with an inner surface that uniformly contacts the entirety of the residual limb surface. In other instances, the customized prosthetic insert socket may contact some portions of the residual limb surface with deliberate spacing from other portions of the residual limb surface.

According to various embodiments of the presently described systems and methods, the customized prosthetic insert socket has an inner contour that conforms to the residual limb surface. However, the customized prosthetic insert socket has a standardized outer surface contour that conforms to an inner contour of one of a set of premade shell sockets. A premade shell socket serves as a rigid shell to reinforce the customized prosthetic insert socket and connect to an artificial limb (e.g., a leg, arm, foot, shank, pylon, or the like). A puck or other attachment device may serve as an attachment interface between the artificial limb and the premade shell socket and/or the customized prosthetic insert socket.

In some embodiments, premade shell sockets may be manufactured in multiple standardized sizes, such as small, medium, and large, or sizes 1-10. The premade shell sockets may be manufactured to provide rigidity to the prosthetic socket. For example, the premade shell sockets may be manufactured from woven fiberglass, woven carbon fiber, filament-wound carbon fiber, filament-wound fiberglass, acrylics, resins, or the like.

The customized prosthetic insert socket may be manufactured using fiberglass, plastic, acrylic, thermoplastic, resin, and/or other material that is, at least temporarily, moldable or flexible. For example, a thermoplastic material may be heated and molded such that an inner contour of the thermoplastic prosthetic insert socket conforms to the residual limb surface contour. The thermoplastic material may then be molded and/or material may be added such that the outer contour of the thermoplastic prosthetic insert socket conforms to the inner surface contour of the premade shell socket, or at least one size of a set of premade shell sockets of various sizes. In some embodiments, the customized prosthetic insert socket may be formed or manufactured by manual fitting or wrapping a material onto the residual limb of a patient. In other embodiments, the customized prosthetic insert socket may be formed or manufactured using a manufacturing process, such as via a casting, extrusion, injection, milling, or molding process.

In other embodiments, the customized prosthetic insert socket may be printed via a three-dimensional printer. For example, a practitioner may use a three-dimensional scanner, an imaging device, or manual measurements to generate a digital three-dimensional residual limb surface contour. The practitioner and/or a computer-implemented system may select one of a plurality of available premade shell sockets based on the size of the patient, one or more dimensions of the digital residual limb surface contour, the prosthetic limb to be utilized with the prosthetic socket (e.g., the pylon), the desired rigidity, and/or the desired look or design.

The system may determine an inner contour of the selected premade shell socket. The practitioner may then cause a three-dimensional printer to print a customized prosthetic insert socket that has an inner contour that conforms to the digital three-dimensional residual limb surface contour and an outer contour that conforms to the inner contour of the selected premade shell socket. The customized prosthetic insert socket may be fitted to the patient, and the selected shell socket may be fitted around the customized prosthetic insert socket to provide rigidity and strength. An artificial limb (e.g., a leg, arm, pylon, foot, hand, or the like) may be attached to a puck or other attachment feature of the shell socket and/or the customized prosthetic insert socket.

According to various embodiments, the customized prosthetic insert socket may be three-dimensionally printed using any of a wide variety of materials suitable for three-dimensional printing. In some embodiments, another material, such as cloth or fiberglass, may be used to line the inner and/or outer surface of the three-dimensional-printed customized prosthetic insert socket. Suitable materials for three-dimensional printing a customized prosthetic insert socket include, but are not limited to, plastics, metals, resins, thermoplastics, ceramics, nylons. Specific examples of suitable materials include ABS, TPE, TPU, PLA, HIPS, PETG, carbon-fiber-infused PLA or ABS, ASA, polycarbonate, polypropylene, or the like. Furthermore, any of a wide variety of three-dimensional printing technologies may be utilized.

In some embodiments, a vacuum assist device may be integrated into the puck or other attachment feature, the shell socket, and/or the customized prosthetic insert socket to remove air between the shell socket and the customized prosthetic insert socket and/or between the customized prosthetic insert socket and the residual limb of the patient. In some embodiments, the vacuum assist device may include one or more valves, such as check valves, to facilitate the removal of the air without allowing air to flow back into the region. An between the prosthetic insert and the shell socket may be utilized to maintain the vacuum seal.

In some embodiments, the customized prosthetic insert socket may be three-dimensionally printed with one or more pockets that each serves as a bladder connected to a perimeter of the three-dimensionally printed prosthetic insert socket via one or more corresponding tubes. Each bladder may be connected with one tube or multiple tubes. Each tube may be three-dimensionally printed as integrated voids in the customized prosthetic insert socket. Alternatively, each tube may comprise a premade tube that is manually inserted (or mechanically inserted by a machine) during the three-dimensional printing process. Each tube may connect the bladder to a pump. The pump may selectively inflate (or fill) and deflate (or empty) each bladder to provide selective spatial compression against the residual limb of the patient.

According to some embodiments, each bladder may be selectively inflated or deflated with a gas, such as air or nitrogen. In other embodiments, each bladder may be selectively filled with or emptied (unfilled) of a fluid, such as oil, silicone, liquid, gas, or the like. Thus, in various embodiments, each bladder may be connected by a tube to a pneumatic pump or hydraulic pump for the selective filling (inflating) and emptying (deflating) of each respective bladder. In some embodiments, two or more bladders may share a common tube and thus be inflated (filled) or deflated (emptied) together. In various embodiments, the bladders may be considered and referred to as inflatable bladders, fluid bladders, pneumatic bladders, pocket bladders, or the like.

In many of the embodiments described herein, electronically controlled pumps are described. However, it is appreciated that manual pumps or other mechanical devices may be used to selectively fill and empty each bladder. For example, mechanical screw devices, manual pumps, levers, gears, check valves, squeezable ball primers, and/or other mechanical devices may be accessible, integrated within, and/or attachable to an interface with the one or more tubes connected to the one or more bladders.

In some embodiments, the pump system may be electronically controlled and/or may interface via a wireless communication module with a portable electronic device, such as a mobile phone. The pump system may be attached to or integrated with a puck system or other attachment feature near the base of the prosthetic socket. The pump system may be battery or capacitively powered. Specific examples of possible embodiments, in simplified illustrations, are illustrated and described herein.

The presently described system allows for rigid outer shell sockets to be premanufactured with known inner surface contours. This approach eliminates the need for a practitioner to custom manufacture or wrap a rigid outer layer of a prosthetic socket. This allows the outer shell socket to be manufactured ahead of time using improved or stronger materials (e.g., filament wound carbon fiber instead of woven carbon fiber fabrics) and decreases the manufacturing time of a custom prosthetic device for a patient. The presently described systems and methods result in a customized prosthetic insert socket that can be mated and unmated with premade, rigid outer shell sockets.

In some embodiments, the outer shell socket can be removed from a customized prosthetic insert socket installed on a patient. Adjustments can then be made to the inner contour of the customized prosthetic insert socket to improve the fit against the residual limb of the patient. The outer shell socket can then be re-fitted around the customized prosthetic insert socket. In other embodiments, the outer shell socket may be permanently secured and fitted to the customized prosthetic insert socket to improve the adhesion therebetween.

In a specific implementation, a multi-layer prosthetic socket includes a premade outer shell socket (e.g., with an asymmetric inner surface contour) and a customized prosthetic insert socket (e.g., three-dimensionally printed) with an outer contour that corresponds to the inner surface contour of the premade outer shell socket. The inner contour of the premade outer shell socket corresponds to a residual limb surface contour of a residual limb of a patient. The outer contour of the customized prosthetic insert socket and the asymmetric inner surface contour of the premade outer shell socket may interact to selectively secure the customized prosthetic insert socket within the premade outer shell socket.

A plurality of bladders formed or otherwise positioned within the prosthetic insert socket may be selectively filled to apply pressure on the residual limb of the patient (e.g., between the residual limb of the patient and the rigid premade outer shell socket). An attachment puck may facilitate the connection of a prosthetic limb to the premade outer shell socket.

In some embodiments, the attachment puck may be integrated within the premade outer shell socket. Thru-bores in the attachment puck may facilitate fastening the premade outer shell socket to the prosthetic insert socket. For example, screws may be screwed into the attachment puck and into reinforced threaded apertures in the prosthetic insert socket.

In some embodiments, a multi-layer prosthetic socket may also include a perspiration collection subsystem configured to trap, direct, wick, or otherwise collect perspiration and expel the perspiration. In some instances, the perspiration may be expelled via a plurality of valves to facilitate the expulsion of the perspiration without breaking a vacuum seal between the residual limb of the patient and the prosthetic insert socket.

Some of the infrastructure that can be used with embodiments disclosed herein is already available, such as general-purpose computers, three-dimensional printers, computer programming tools and techniques, digital storage media, virtual computers, electronic pumps, prosthetic limps, virtual networking and wireless devices, and other communications networks.

Aspects of certain embodiments described herein may be implemented as software modules or components. For example, the three-dimensional printing system may utilize software and/or hardware modules to manage the scanning of a residual limb, generate a digital residual limb surface contour, print a customized prosthetic insert socket, and/or form voids (e.g., not printing material or removing material) within a customized prosthetic insert socket to function as inflatable or fillable bladders for connection to a manual or electronic pump. As used herein, a software module or component may include any type of computer instruction or computer-executable code located within or on a computer-readable storage medium. A software module may, for instance, comprise one or more physical or logical blocks of computer instructions, which may be organized as a routine, program, object, component, data structure, etc., that perform one or more tasks or implement particular abstract data types.

A particular software module may comprise disparate instructions stored in different locations of a computer-readable storage medium, which together implement the described functionality of the module. Indeed, a module may comprise a single instruction or many instructions and may be distributed over several different code segments, among different programs, and across several computer-readable storage media. Some embodiments may be practiced in a distributed computing environment where tasks are performed by a remote processing device linked through a communications network. In a distributed computing environment, software modules may be located in local and/or remote computer-readable storage media. In addition, data being tied or rendered together in a database record may be resident in the same computer-readable storage medium, or across several computer-readable storage media, and may be linked together in fields of a record in a database across a network.

The embodiments of the disclosure can be understood by reference to the drawings, wherein like parts are designated by like numerals throughout. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments. In other instances, well-known structures, materials, or operations are not shown or described in detail to avoid obscuring aspects of this disclosure. In addition, the steps of a method do not necessarily need to be executed in any specific order, or even sequentially, nor need the steps be executed only once, unless otherwise specified.

FIG. 1A illustrates an example of a three-dimensional scanner 110 used to scan a residual limb 155 of a patient 150. The three-dimensional scanner 110 may be connected (e.g., wirelessly or via a wire) to a computing system and used to generate a digital three-dimensional residual limb surface contour 175, according to various embodiments. While the example illustration shows a residual limb 155 of a leg of the user 150, it is appreciated that the systems and methods described herein may be applied to other residual limbs and/or other portions of the body of the user 150.

Figure 1B:
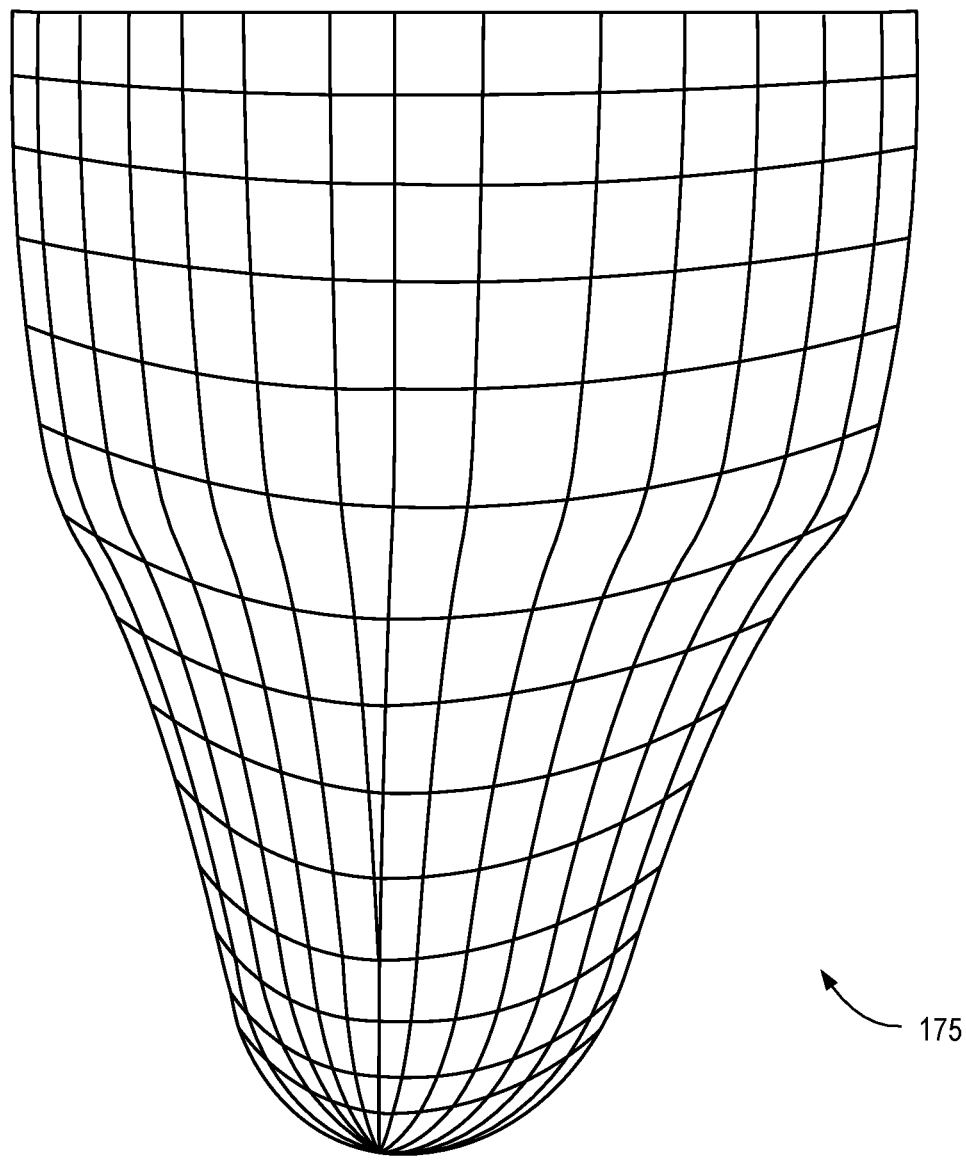
FIG. 1B illustrates an example of a digital three-dimensional residual limb surface contour, according to one embodiment.

FIG. 1B illustrates an example of a digital three-dimensional residual limb surface contour 175 in a wireframe format, according to various embodiments. In some examples, manual measurements and/or other inputs may be provided by the practitioner and used by the system to modify or adjust the digital three-dimensional residual limb surface contour 175.

Figure 2:
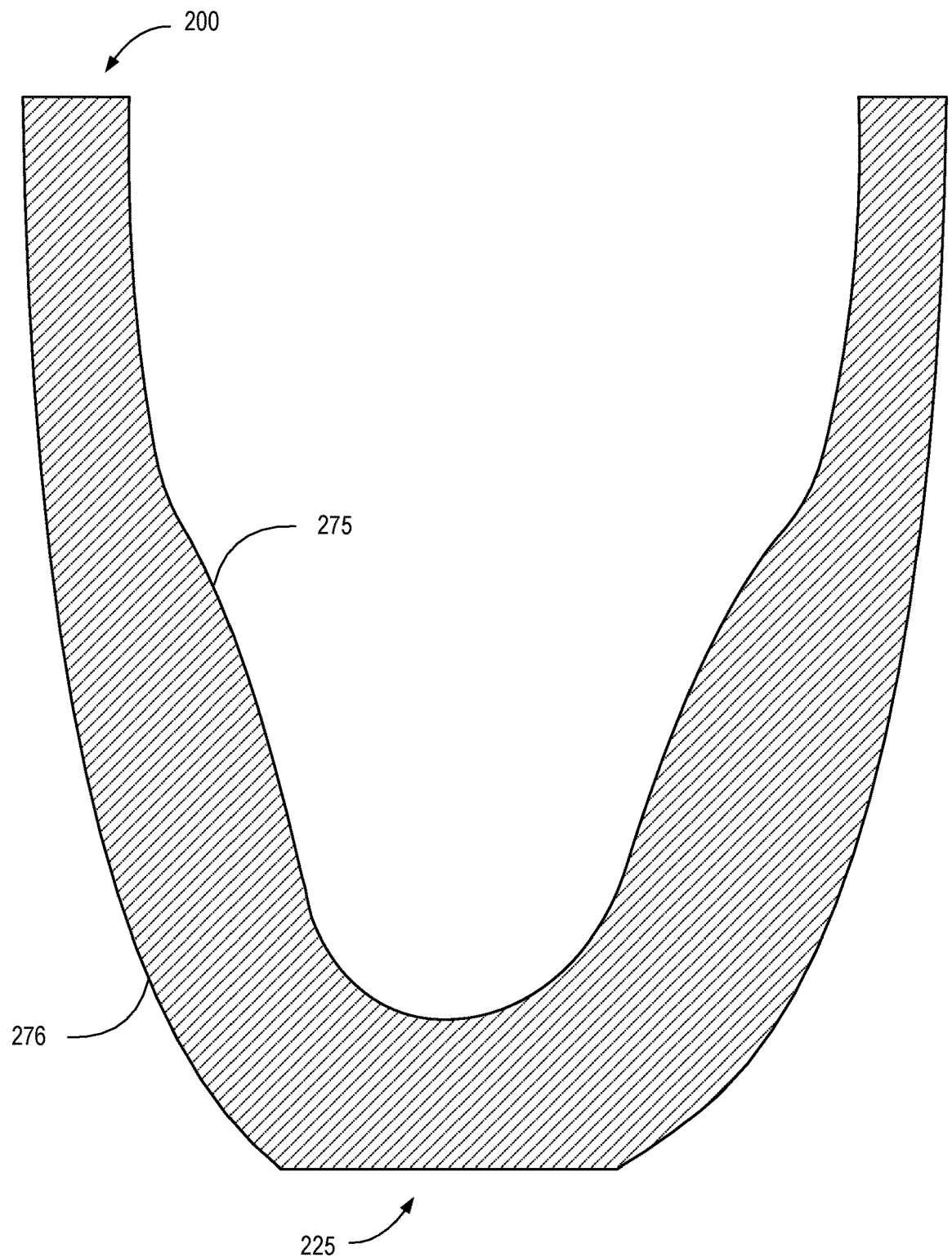
FIG. 2 illustrates a cross-sectional view of an example of a customized prosthetic insert socket with an inner contour conforming to the residual limb surface contour, according to one embodiment.

FIG. 2 illustrates a cross-sectional view of an example of a customized prosthetic insert socket 200 with an inner surface contour 275 that conforms to a residual limb surface contour, such as the residual limb surface contour 175 illustrated in FIG. 1B. As described herein, the customized prosthetic insert socket 200 may be printed with a three-dimensional printer. In various embodiments, the outer surface contour 276 of the customized prosthetic insert socket 200 may be printed to conform to the inner surface contour of a premade shell socket. Accordingly, the wall thickness of the customized prosthetic insert socket 200 may vary as needed to allow for both the inner surface contour 275 and outer surface contour 276 to conform to the residual limb surface contour and the inner surface contour of a premade shell socket, respectively.

In various embodiments, the base portion 225 of the customized prosthetic insert socket 200 may have a varying thickness and shape to conform to a base portion of an inner surface contour of a premade shell socket. In some examples, the customized prosthetic insert socket 200 may include an integrated puck or another attachment interface for securing the customized prosthetic insert socket 200 to a prosthetic limb (e.g., a pylon).

Figure 3A:
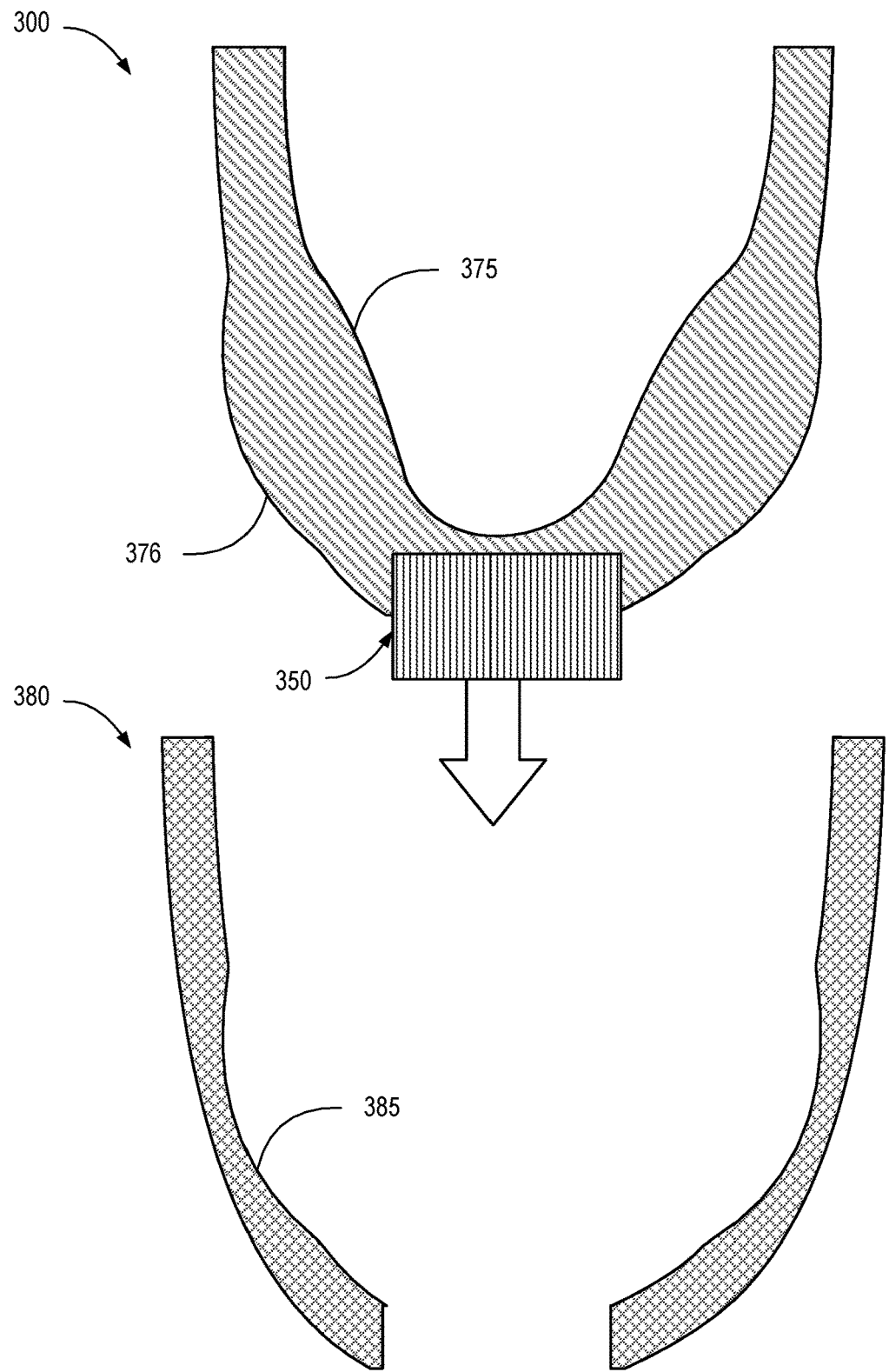
FIG. 3A illustrates a cross-sectional view of an example of a multi-piece prosthetic socket with a customized prosthetic insert socket that has an integrated attachment puck, according to one embodiment.

FIG. 3A illustrates a cross-sectional view of an example of a multi-piece prosthetic socket with a customized prosthetic insert socket 300 having an integrated attachment puck 350. The prosthetic insert socket 300 includes an inner surface contour 375 conforming to the residual limb surface contour and an outer contour 376 conforming to the inner contour 385 of a premade outer shell socket 380, according to one embodiment.

Figure 3B:
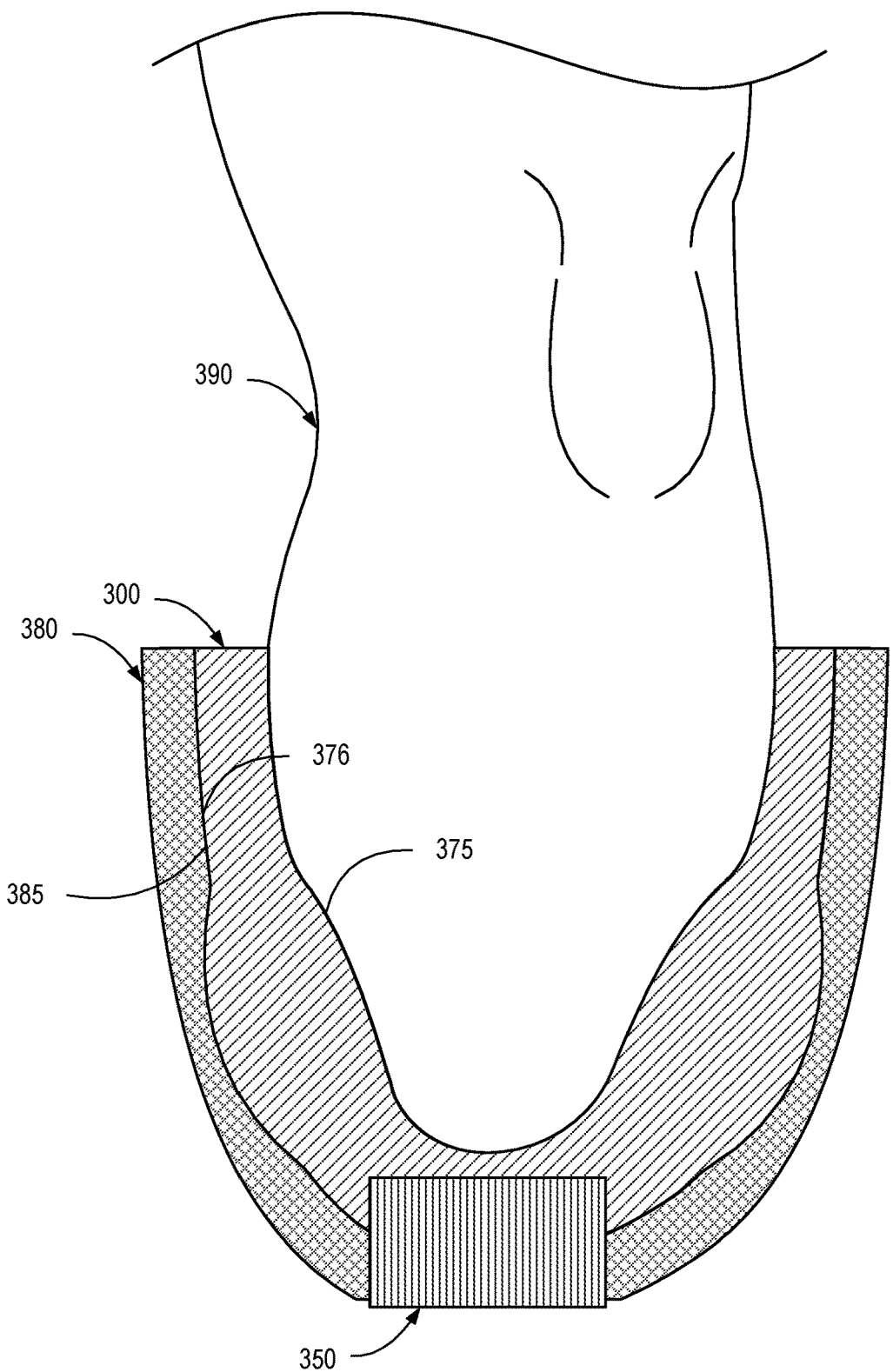
FIG. 3B illustrates a cross-sectional view of an example of a residual limb within the multi-piece prosthetic socket comprising the customized prosthetic insert socket with the integrated attachment puck and a premade outer shell socket, according to one embodiment.

FIG. 3B illustrates a cross-sectional view of an example of a residual limb 390 within the multi-piece prosthetic socket comprising the customized prosthetic insert socket 300 with the integrated attachment puck 350 and the premade outer shell socket 380, according to one embodiment.

Figure 4A:
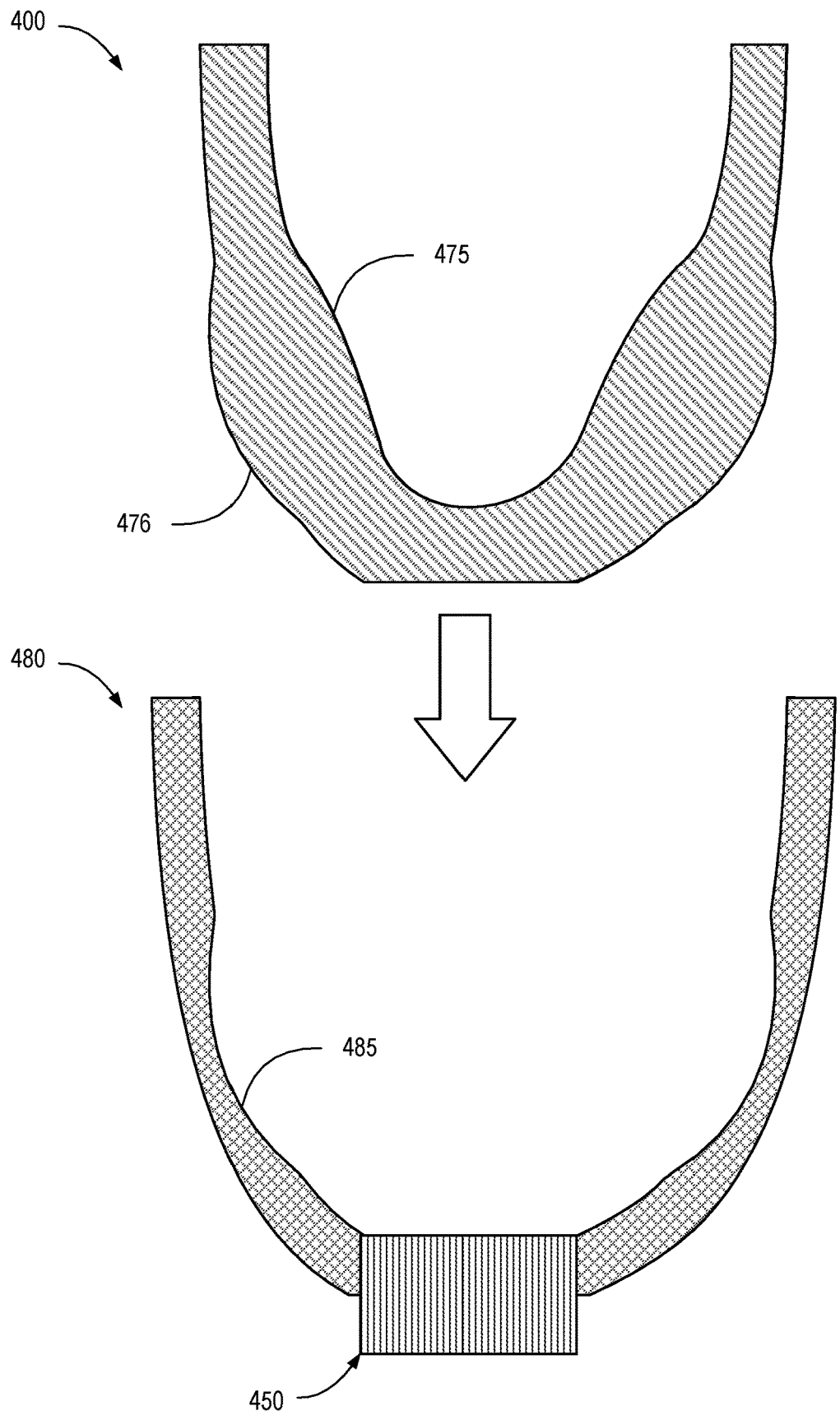
FIG. 4A illustrates a cross-sectional view of an example of a customized prosthetic insert socket with an inner contour conforming to a residual limb surface contour and an outer contour conforming to the inner contour of a premade outer shell socket with an integrated attachment puck, according to one embodiment.

FIG. 4A illustrates another example of a customized prosthetic insert socket 400 with an inner surface contour 475 conforming to a residual limb surface contour (e.g., the residual limb surface contour 175 illustrated in FIG. 1B). The outer surface contour 476 may be manufactured (e.g., three-dimensional printed) to conform to the inner surface contour 485 of a premade outer shell socket 480. The premade outer shell socket 480 may be one of a plurality of different sizes of premade outer shell sockets available to the practitioner. In the illustrated embodiment, an attachment puck 450 for attaching a lower prosthetic limb (e.g., a prosthetic knee or pylon) is integrated with the premade outer shell socket 480.

According to various embodiments, the inner surface contour 485 of the premade outer shell socket 480 may have curves, depressions, protrusions, and/or other surface features to capture and/or secure the customized prosthetic insert socket 400. In some embodiments, the premade outer shell socket 480 may include external structures to tighten the premade outer shell socket 480 around the customized prosthetic insert socket 400. For example, laces, buckles, straps, or other external structures may be used to tighten the premade outer shell socket 480 around the customized prosthetic insert socket 400 and the residual limb of the patient.

Figure 4B:
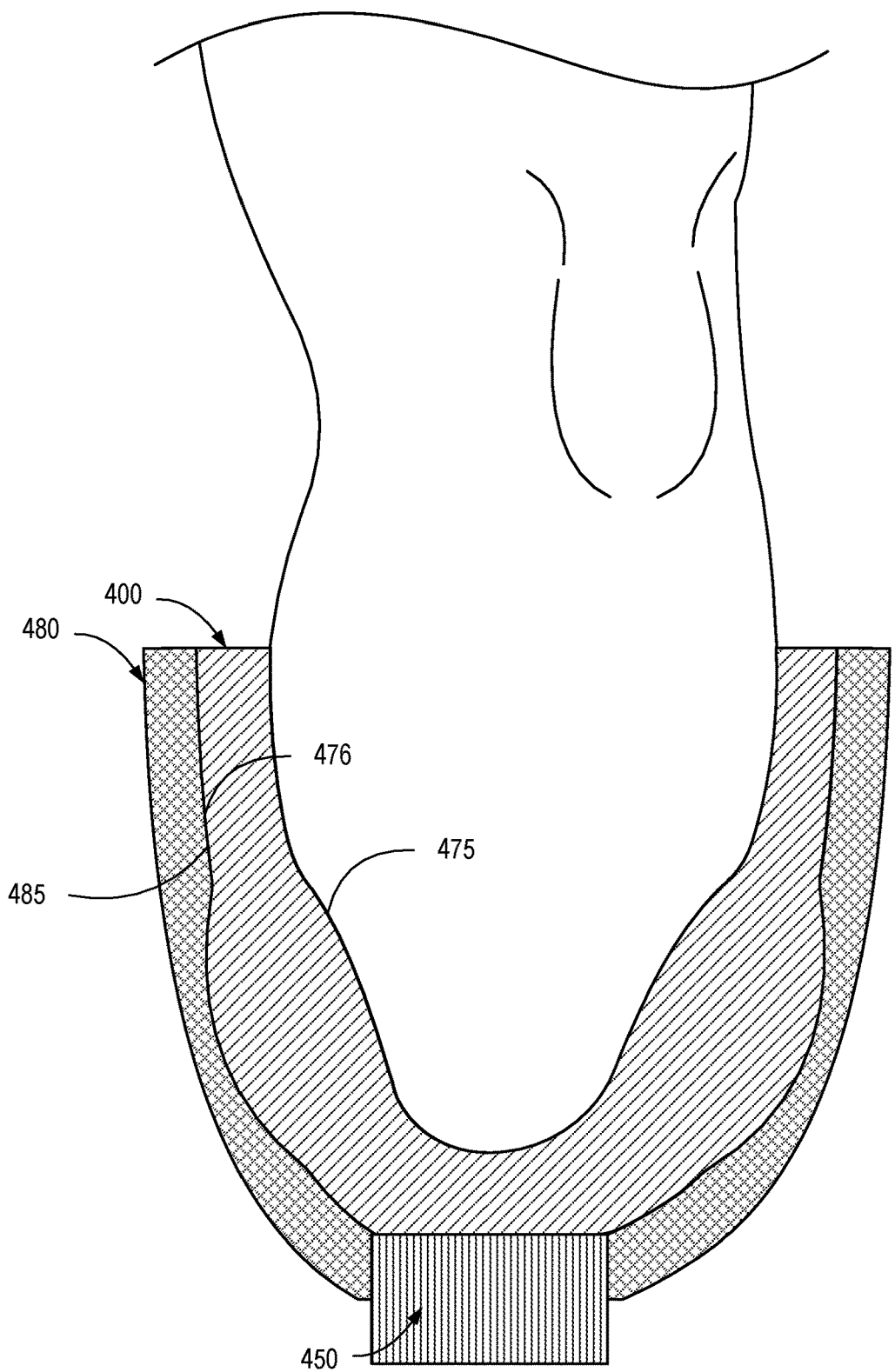
FIG. 4B illustrates a cross-sectional view of an example of a residual limb within the multi-piece prosthetic socket comprising the customized prosthetic insert socket and the premade outer shell socket with the integrated attachment puck, according to one embodiment.

FIG. 4B illustrates another example of the customized prosthetic insert socket 400 of FIG. 4A with an integrated attachment puck 450, according to an alternative embodiment. As illustrated, the attachment puck 450 is accessible through the bottom of the premade outer shell socket 480 once the customized prosthetic insert socket 400 is inserted therein.

Figure 5A:
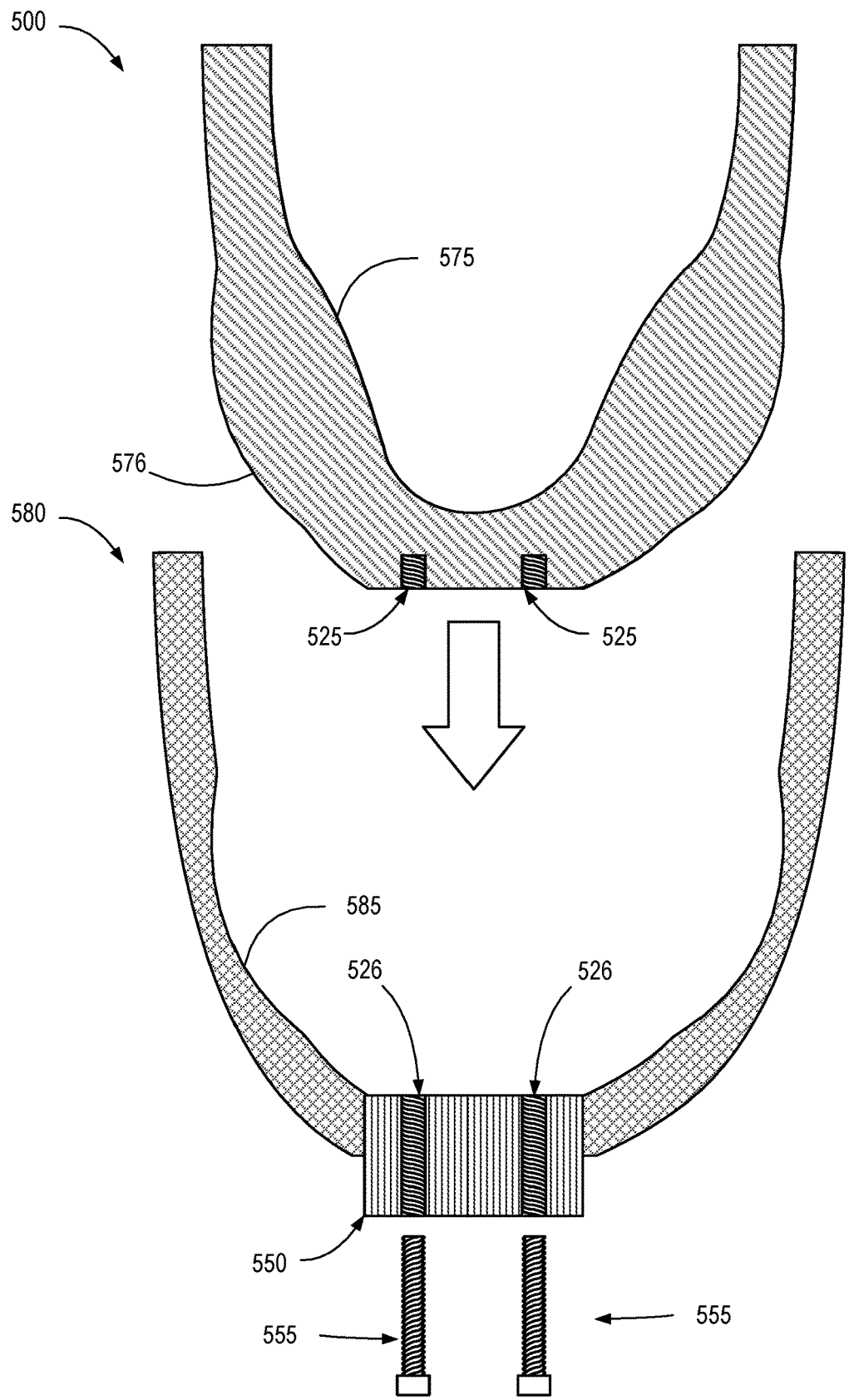
FIG. 5A illustrates a cross-sectional view of an example of a multi-piece prosthetic socket with thru-bore attachment features, according to one embodiment.

FIG. 5A illustrates a cross-sectional view of an example of a multi-piece prosthetic socket with thru-bore attachment features 525 and 526, according to one embodiment. Again, the customized prosthetic insert socket 500 includes an inner surface contour 575 that conforms to the exterior surface contour of a residual limb of a patient. An outer surface contour 576 of the prosthetic insert socket 500 is configured to conform to the asymmetrical inner surface contour 585 of the premade outer shell socket 580.

The attachment puck 550 for attaching a lower prosthetic limb is integrated within the premade outer shell socket 580 and includes thru-bore attachment features 526 to receive fasteners 555. For example, fasteners 555 may be configured to thread into thru-bore attachment features 526. The prosthetic insert socket 500 may include threaded fastener receivers 525 as well. The fasteners 555 may be used to secure the prosthetic insert socket 500 to the premade outer shell socket 580.

Figure 5B:
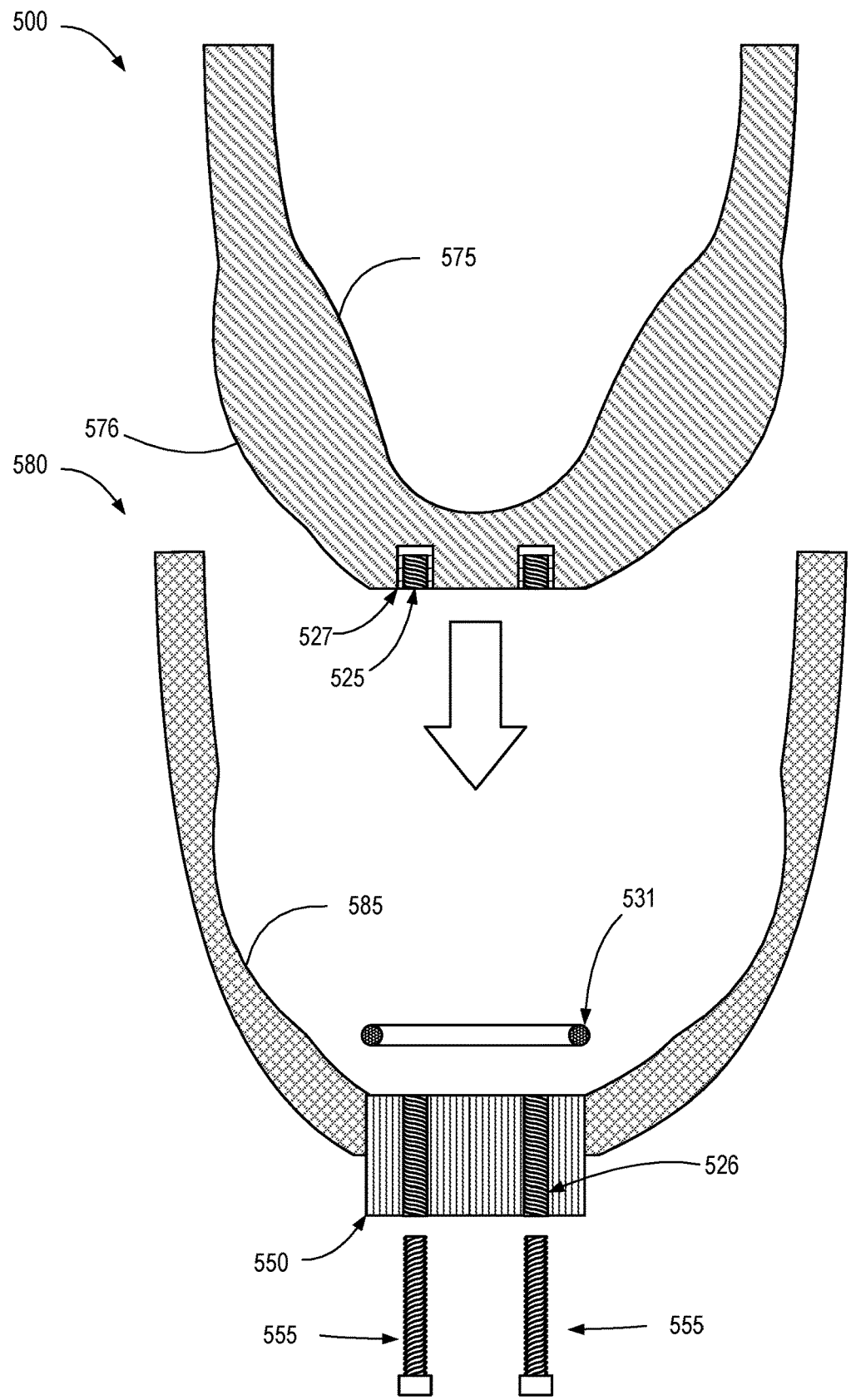
FIG. 5B illustrates a cross-sectional view of an example of a multi-piece prosthetic socket with reinforced thru-bore attachment features, according to one embodiment.

FIG. 5B illustrates a cross-sectional view of an example of the multi-piece prosthetic socket with reinforced thru-bore attachment features, according to one embodiment. As illustrated, the threaded fastener receivers 525 are reinforced with a reinforcement material 527 that is different from the material used to, for example, three-dimensionally print the prosthetic insert socket 500. The multi-piece prosthetic socket may further include one or more O-rings 531 to be seated between the prosthetic insert socket 500 and the premade outer shell socket 580. In the illustrated embodiment, the O-ring 531 is positioned toward the bottom of the premade outer shell socket 580. However, it is appreciated that the O-ring 531 or additional O-rings may be positioned in other locations (e.g., higher up toward the top) between the prosthetic insert socket 500 and the premade outer shell socket 580.

Figure 5C:
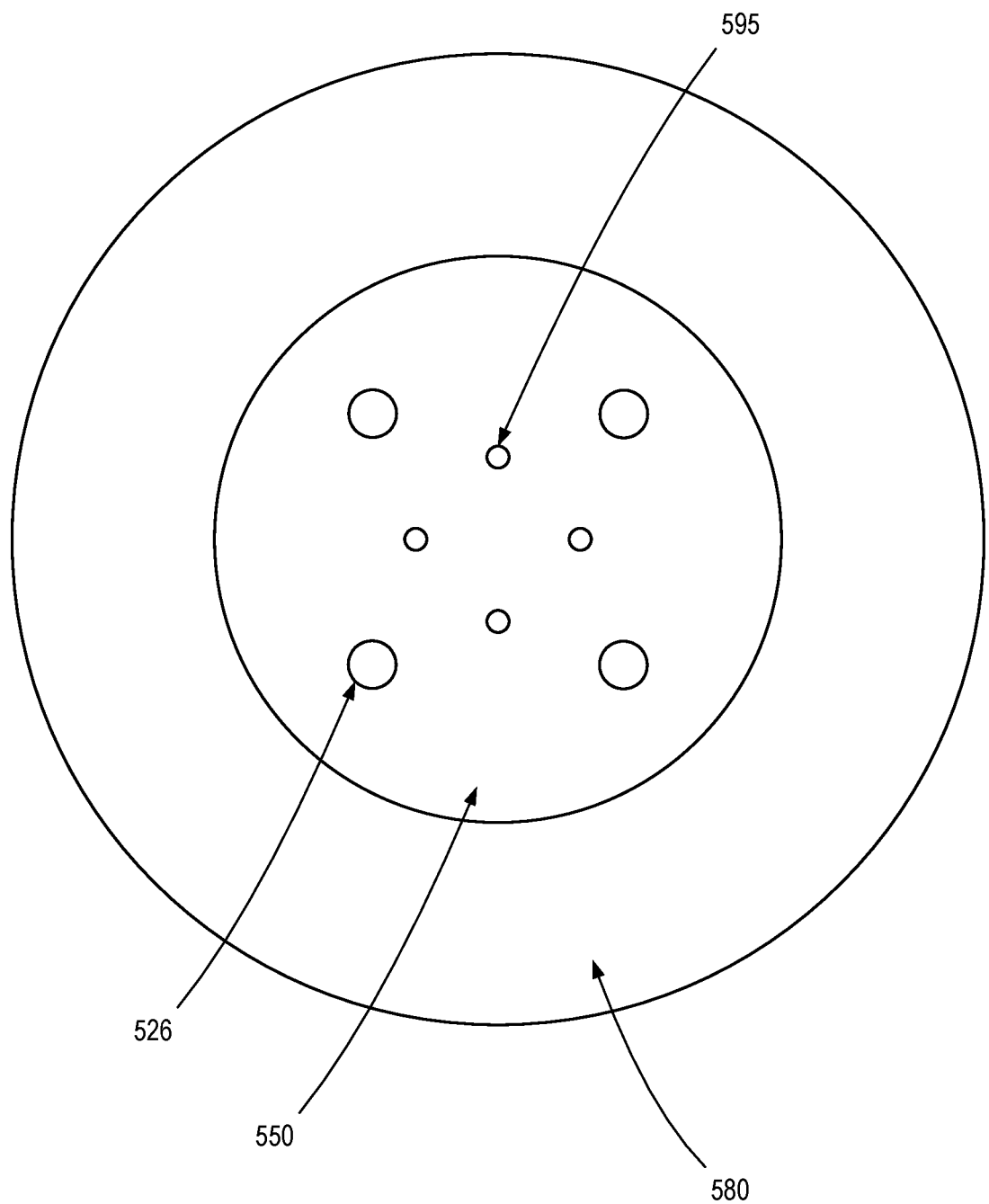
FIG. 5C illustrates a bottom view of a multi-piece prosthetic socket with thru-bore attachment features, according to one embodiment.

FIG. 5C illustrates a bottom view of a multi-piece prosthetic socket with thru-bore attachment features 526 in the attachment puck 550 integrated within the premade outer shell socket 580, according to one embodiment. In various embodiments, the attachment puck 550 may include additional attachment features 595 to facilitate the attachment of a prosthetic limb to the multi-piece prosthetic socket.

Figure 5D:
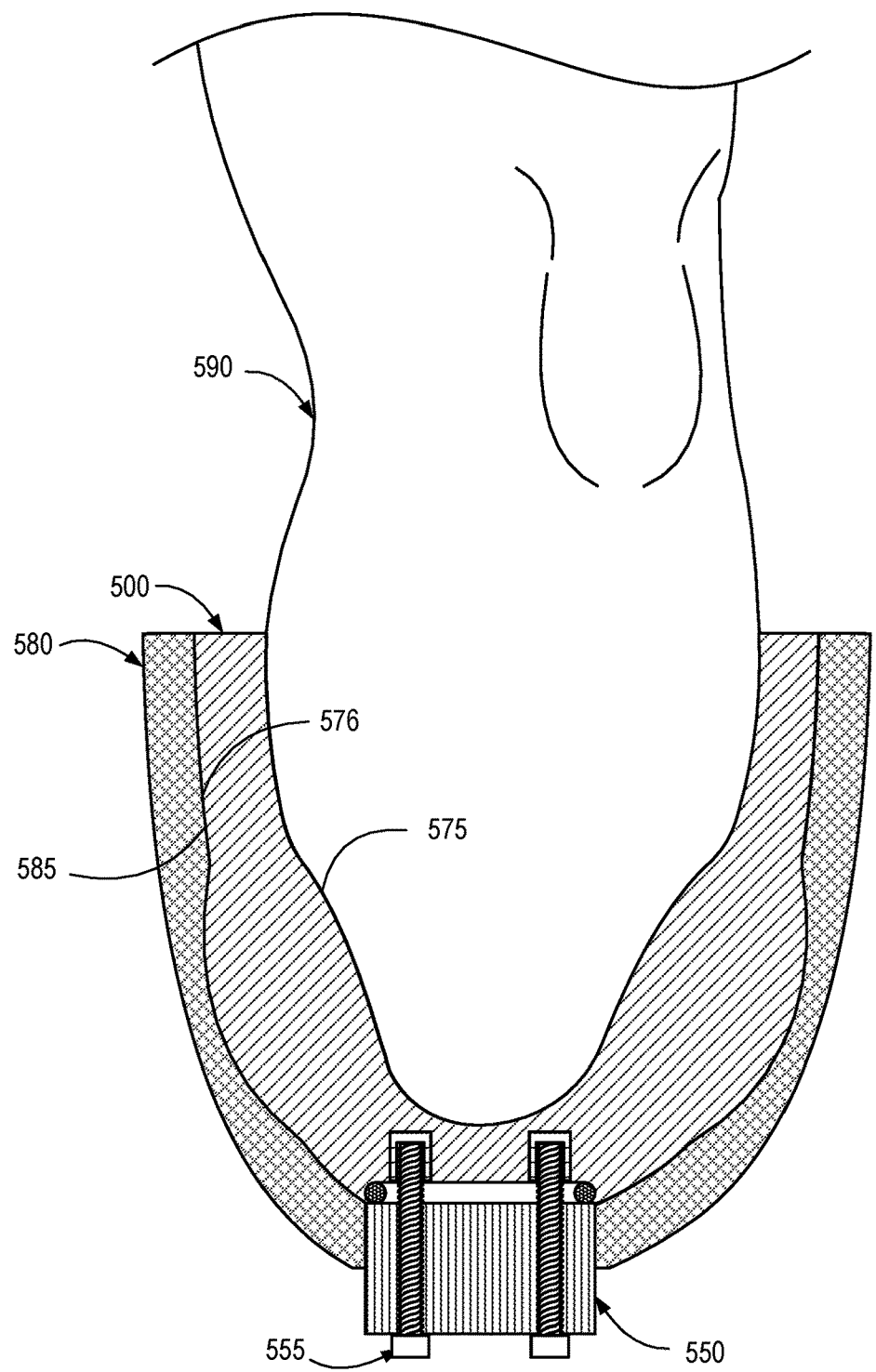
FIG. 5D illustrates a cross-sectional view of an example of a residual limb within the multi-piece prosthetic socket with reinforced thru-bore attachment features, according to one embodiment.

FIG. 5D illustrates a cross-sectional view of an example of a residual limb 590 within the multi-piece prosthetic socket with reinforced thru-bore attachment features, as described in FIGS. 5A-5C, according to one embodiment. As illustrated, the fasteners 555 are used to secure the components of the multi-piece prosthetic socket via the thru-bores and reinforced receivers in the attachment puck 550 and prosthetic insert socket 500, respectively.

Figure 6A:
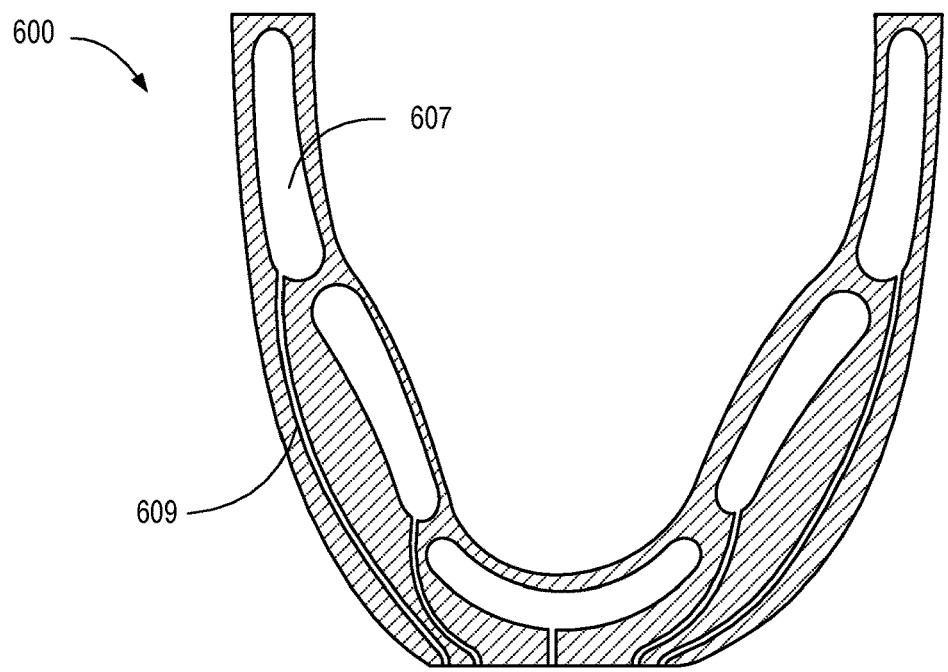
FIG. 6A illustrates a cross-sectional view of another example of a multi-piece prosthetic socket in which the customized prosthetic insert socket includes integrated bladders, according to one embodiment.
Figure 6A:
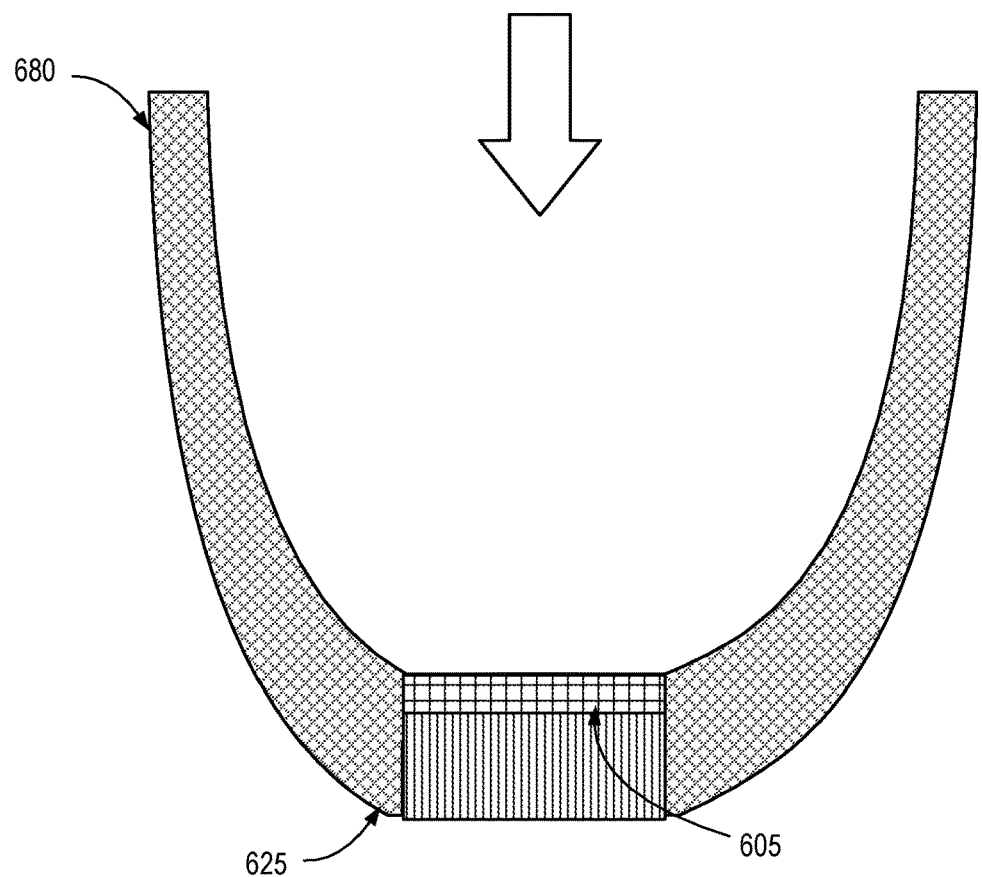

FIG. 6A illustrates a cross-sectional view of another example of a multi-piece prosthetic socket with a customized prosthetic insert socket 600 and a premade outer shell socket 680. As illustrated, the customized prosthetic insert socket 600 includes integrated bladders 607 (five of which are visible) formed as pockets or voids within the customized prosthetic insert socket 600 that are connected to a pump 605 via integrated tubes 609. For example, the customized prosthetic insert socket 600 may be three-dimensionally printed with voids in the printed material that form the bladders 607 and/or the integrated tubes 609. In other embodiments, premade bladders 607 and/or the tubes 609 may be physically positioned during the three-dimensional printing process (or another manufacturing process).

The pump 605 may be manually or electronically actuated to inflate and/or deflate (or fill and empty) the bladders to increase or decrease the pressure against target portions of the residual limb 690. Inflating or filling the bladders 607 increases pressure against portions of the residual limb 690 due to the rigidity of the premade outer shell socket 680. Any number of bladders 607 may be formed in the customized prosthetic insert socket 600. The pump 605 may be used to individually and selectively inflate (or fill) or deflate (or empty) each of the bladders 607 to allow for customized and variable pressure against the residual limb 690. The pump 605 may be a separate component from the attachment puck 625. Alternatively, and as illustrated, the pump 605 may be integrated within a portion of the attachment puck 625.

Figure 6B:
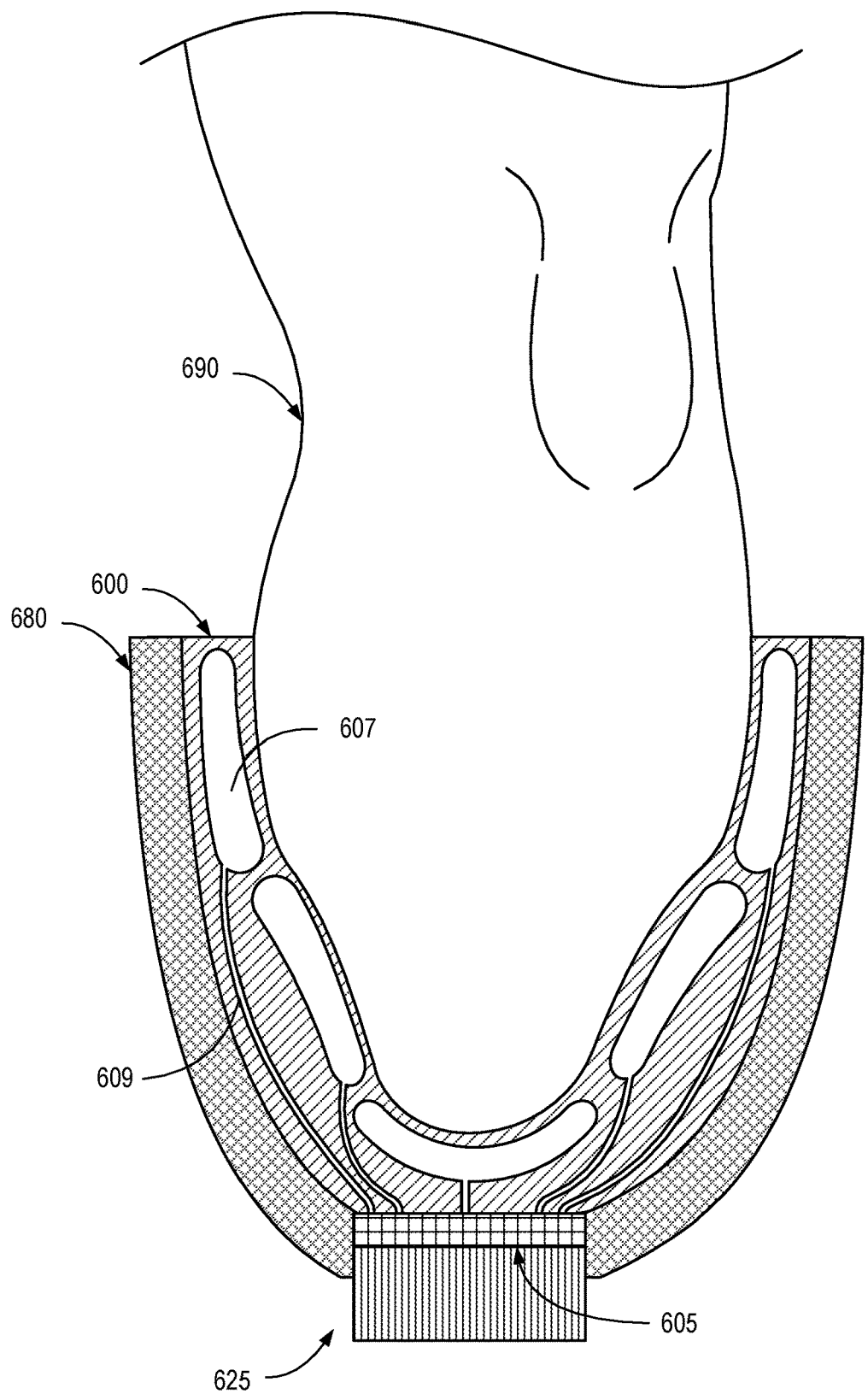
FIG. 6B illustrates a cross-sectional view of an example of a residual limb within the multi-piece prosthetic socket with integrated bladders in the prosthetic insert socket, according to one embodiment.

FIG. 6B illustrates a perspective view of the example multi-piece prosthetic socket of FIG. 6A with the integrated bladders 607 within the customized prosthetic insert socket 600. The outer surface of the customized prosthetic insert socket 600 conforms to the inner surface of the premade outer shell socket 680. Tubes 609 provide a connection between each of the illustrated bladders 607 and the pump 605 integrated within the attachment puck 625. In some embodiments, larger or smaller bladders may be used and/or fewer or more bladders may be used. Furthermore, the bladders 607 may be positioned in any location within the customized prosthetic insert socket 600.

In some alternative embodiments, the bladders may be external to the customized prosthetic insert socket 600. For example, one or more bladders may be positioned between the customized prosthetic insert socket 600 and the residual limb 690 of the patient. In another alternative embodiment, one or more bladders may be positioned between the customized prosthetic insert socket 600 and the premade outer shell socket 680. In still another alternative embodiment, one or more bladders may be positioned within cavities formed in the premade outer shell socket 680 with tubes running between the premade outer shell socket 680 and the customized prosthetic insert socket 600 or within the wall of the premade outer shell socket 680.

Figure 6C:
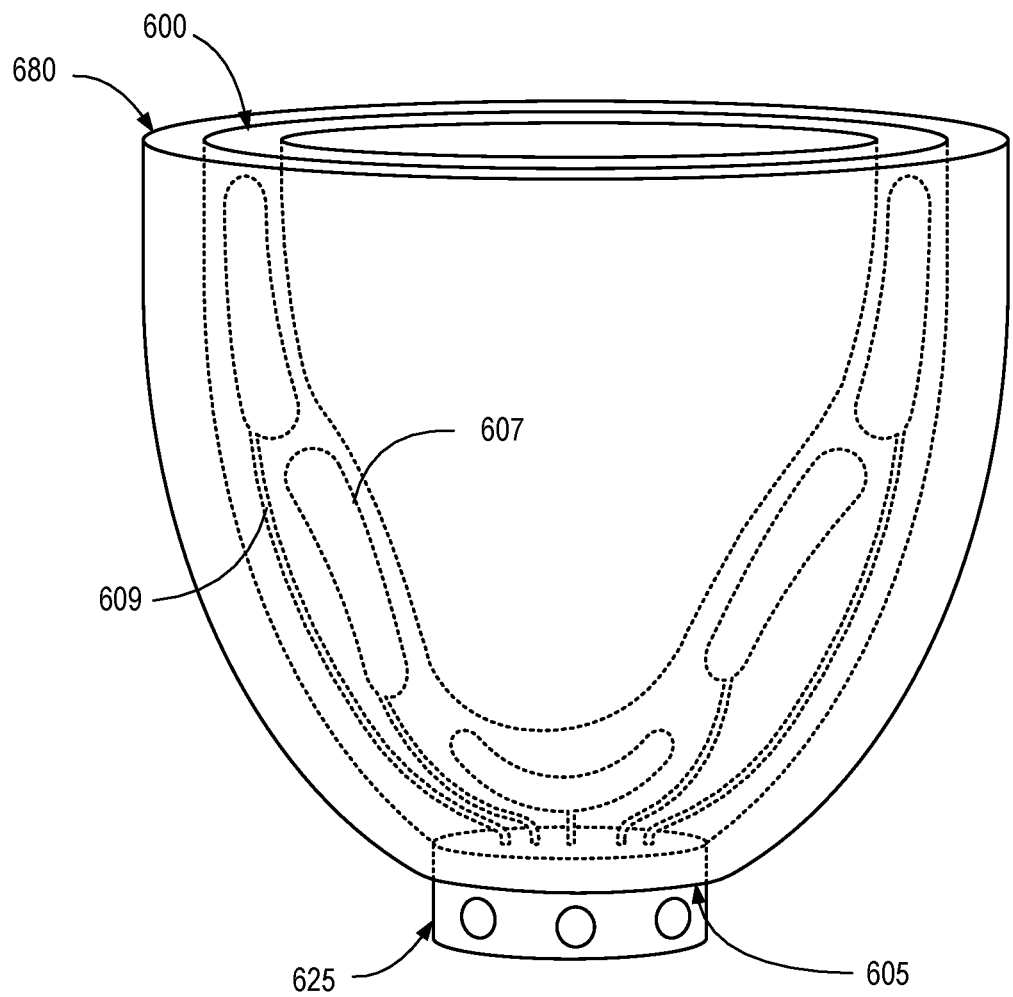
FIG. 6C illustrates a perspective view of the example multi-piece prosthetic socket of FIGS. 6A and 6B with the integrated bladders in dashed lines, according to one embodiment.

FIG. 6C illustrates an example of a two-piece prosthetic socket comprising a customized prosthetic insert socket 600 and a premade outer shell socket 680, according to one embodiment. As illustrated, an attachment puck 625 is accessible for attaching a prosthetic limb. The customized prosthetic insert socket 600 has an inner surface contour 675 that conforms to the surface 694 of the residual limb 690 of the patient. The customized prosthetic insert socket 600 also has an outer surface contour 676 that conforms to the inner surface contour 685 of the premade outer shell socket 680.

Figure 6D:
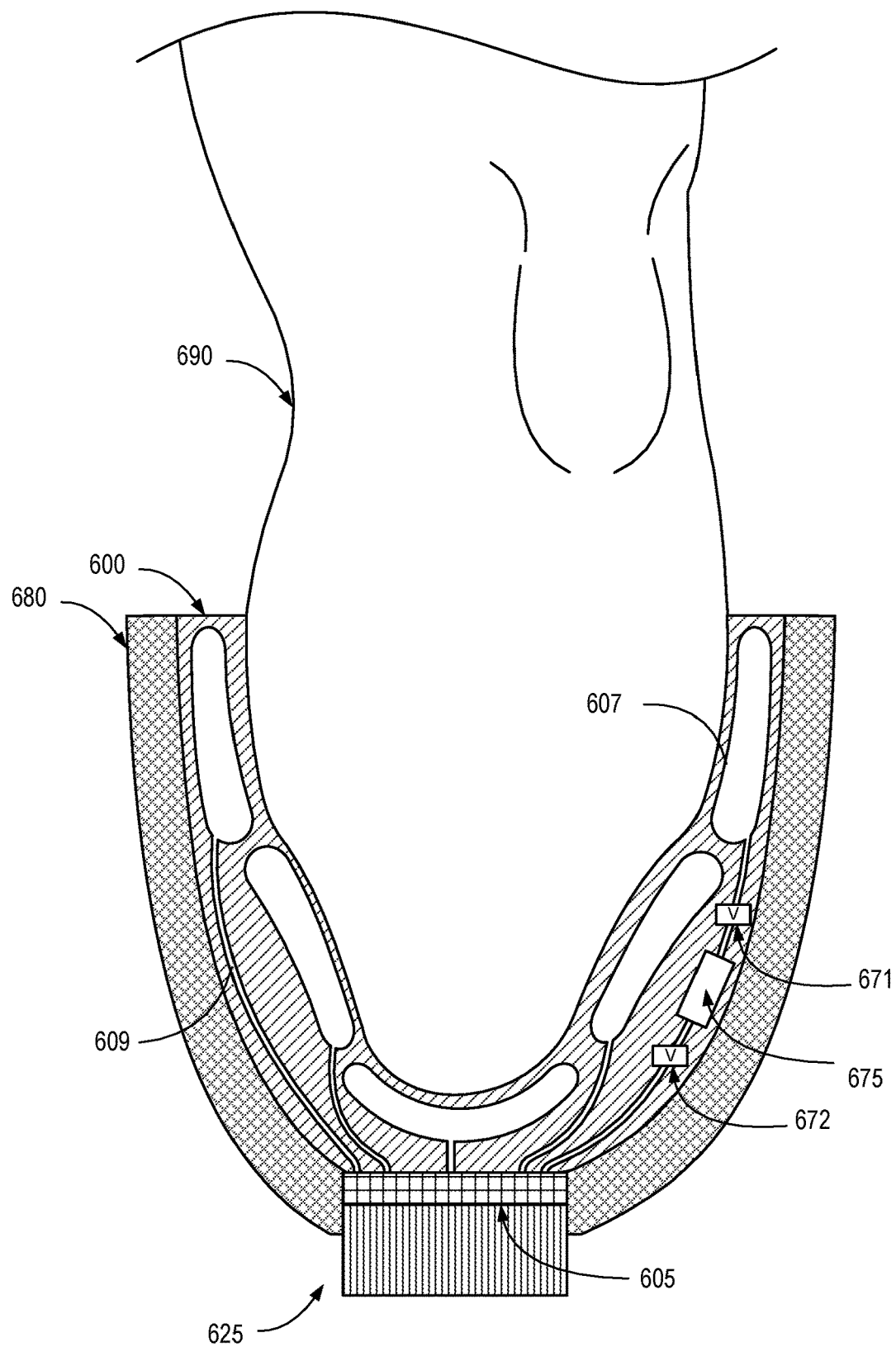
FIG. 6D illustrates a cross-sectional view of an example of a residual limb within the multi-piece prosthetic socket with an integrated bladder that includes a valve-controlled reservoir, according to one embodiment.

FIG. 6D illustrates a cross-sectional view of an embodiment of the multi-piece prosthetic socket in which one or more of the integrated bladders 607 includes valves 671 and 672 that maintain pressure in the bladders 607 using a valve-controlled reservoir 675, according to one embodiment.

Figure 6E:
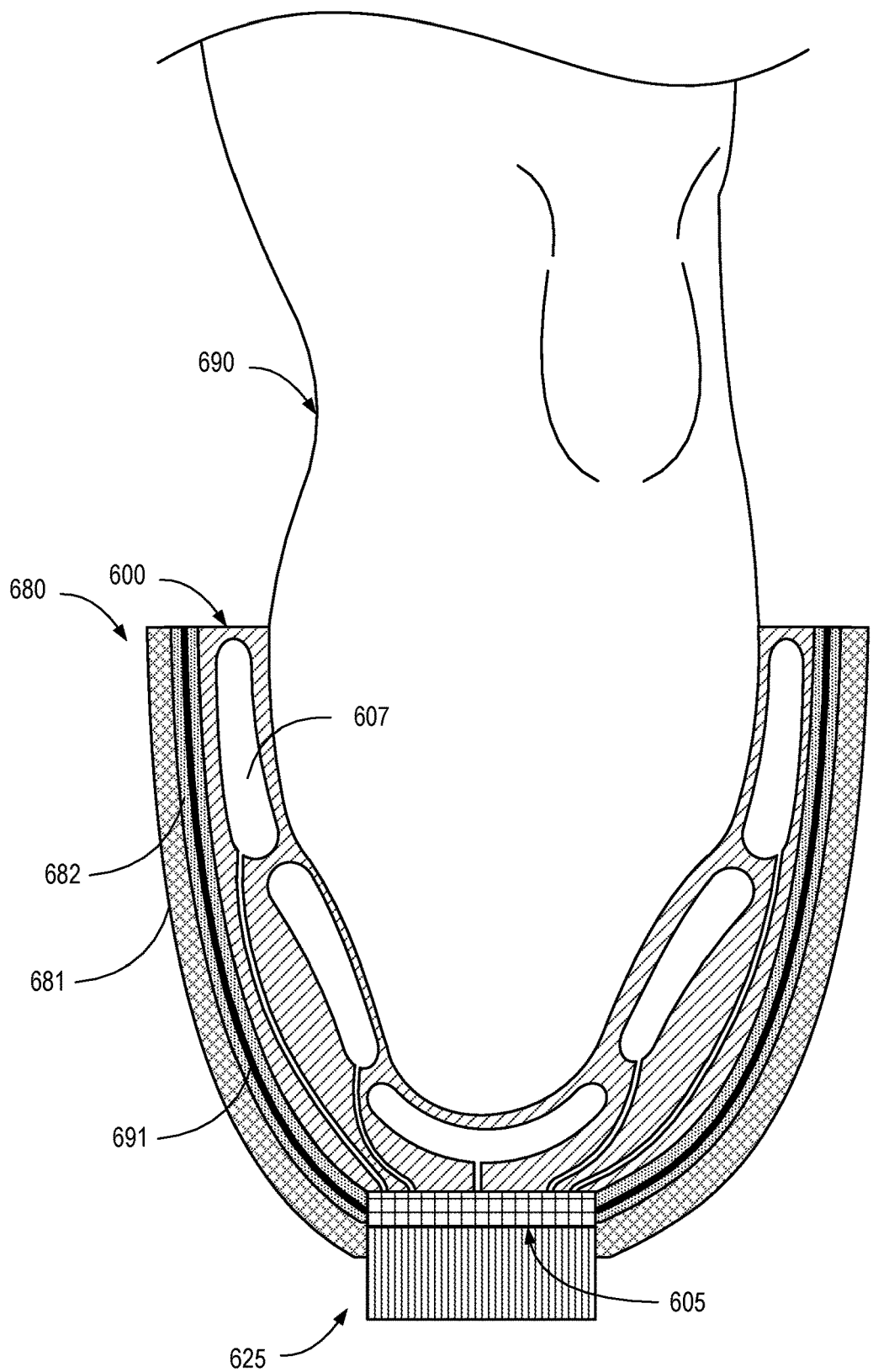
FIG. 6E illustrates a cross-sectional view of an example of a residual limb within the multi-piece prosthetic socket with integrated bladders and a two-layer outer shell socket with integrated sensors, according to one embodiment.

FIG. 6E illustrates a cross-sectional view of a multi-piece prosthetic socket with integrated bladders 607 and a two-layer outer shell socket 680. The two-layer outer shell socket 680 includes a rigid outer layer 681 to provide stability and rigidity and a flexible inner layer 682 that includes one or more sensors, such as a flexible wire sensor 691. A control system (e.g., integrated as a part of or attached to the multi-piece prosthetic socket) may include a processor, memory, and/or a computer-readable memory with instructions stored thereon to cause the control system to modify and control the fluid pressure in the bladders 607.

Figure 6F:
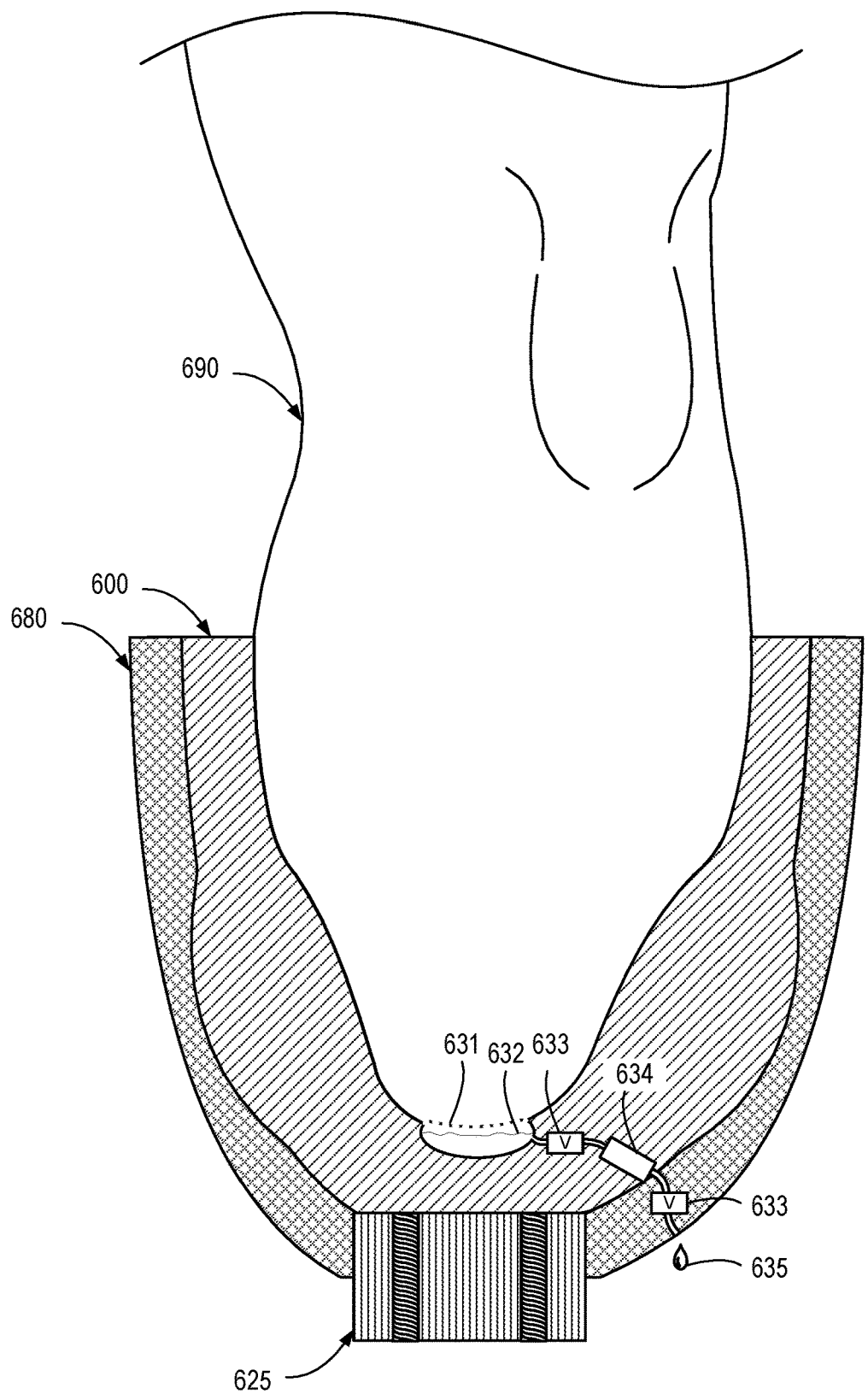
FIG. 6F illustrates a cross-sectional view of an example of a residual limb within the multi-piece prosthetic socket with a valve-controlled sweat relief feature, according to one embodiment.

FIG. 6F illustrates a cross-sectional view of an example of a multi-piece prosthetic socket with a valve-controlled sweat relief feature, according to one embodiment. As illustrated, a water-permeable base layer 631 allows perspiration to accumulate within a perspiration well 632. The sweat relief feature may utilize valves 633 and an intermediary storage region 634 to expel perspiration 635 without breaking a vacuum seal of the multi-piece prosthetic socket.

Figure 7A:
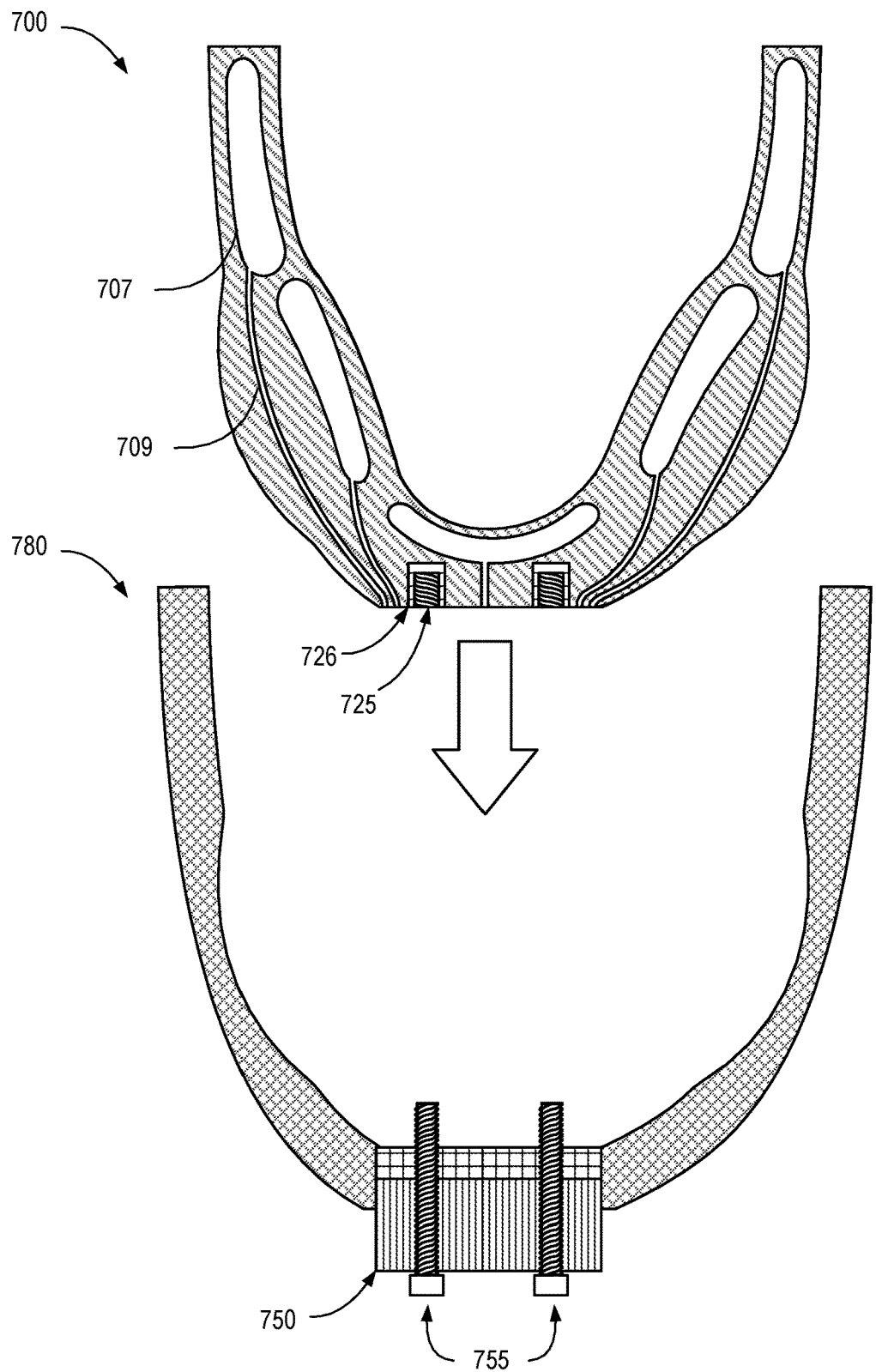
FIG. 7A illustrates a cross-sectional view of another example of a multi-piece prosthetic socket in which the customized prosthetic insert socket includes integrated bladders and reinforced thru-bore attachment features, according to one embodiment.

FIG. 7A illustrates a cross-sectional view of another example of a multi-piece prosthetic socket in which the customized prosthetic insert socket 700 includes integrated bladders 707 and reinforced thru-bore attachment features 725, according to one embodiment. The multi-piece prosthetic socket includes a customized prosthetic insert socket 700 and a premade outer shell socket 780. As illustrated, the customized prosthetic insert socket 700 includes integrated bladders 707 (five of which are visible) formed as pockets or voids within the customized prosthetic insert socket 700 that are connected to a pump 705 via integrated tubes 709.

For example, the customized prosthetic insert socket 700 may be three-dimensionally printed with voids in the printed material that form the bladders 707 and/or the integrated tubes 709. In other embodiments, premade bladders 707 and/or the tubes 709 may be physically positioned during the three-dimensional printing process (or another manufacturing process). The pump 705 may be manually or electronically actuated to inflate and/or deflate (or fill and empty) the bladders 707 to increase or decrease the pressure against target portions of the residual limb 790.

The multi-piece prosthetic socket may also include thru-bore attachment features in the outer shell socket 780 to receive fasteners 755. The prosthetic insert socket 700 may include reinforced threaded attachment features 725 that are reinforced with a material 726 stronger (e.g., more rigid, stiffer, and/or otherwise exhibiting different mechanical or material properties).

Figure 7B:
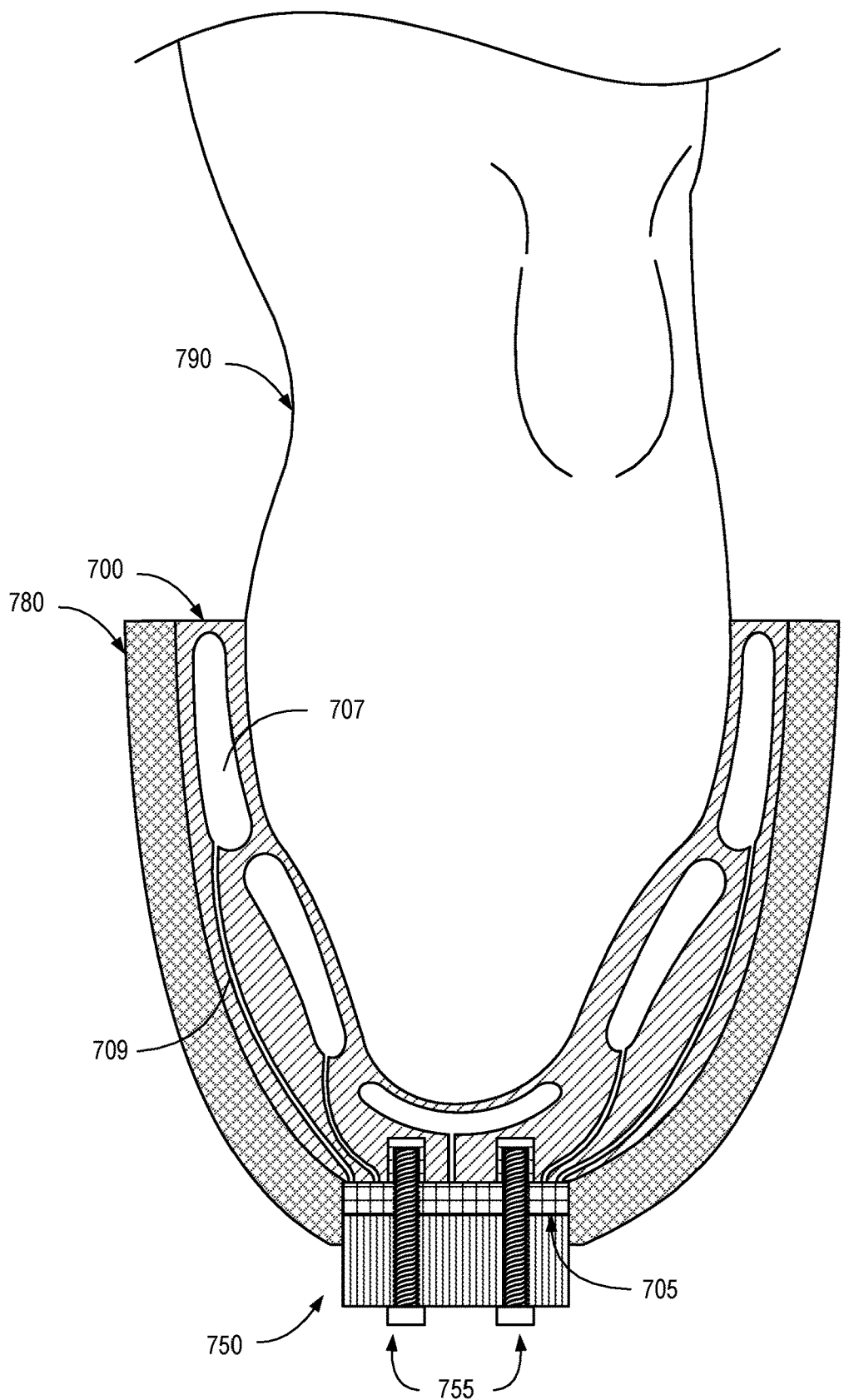
FIG. 7B illustrates a cross-sectional view of an example of a residual limb within the multi-piece prosthetic socket with integrated bladders and reinforced thru-bore attachment features in the prosthetic insert socket, according to one embodiment.

FIG. 7B illustrates a cross-sectional view of an example of a residual limb 790 within the multi-piece prosthetic socket with integrated bladders 707 and reinforced thru-bore attachment features in the prosthetic insert socket 700, according to one embodiment. The outer surface of the customized prosthetic insert socket 700 conforms to the inner surface of the premade outer shell socket 780. Tubes 709 provide a connection between each of the illustrated bladders 707 and the pump 705 integrated within the attachment puck 750. In some embodiments, larger or smaller bladders may be used and/or fewer or more bladders may be used.

Figure 8:
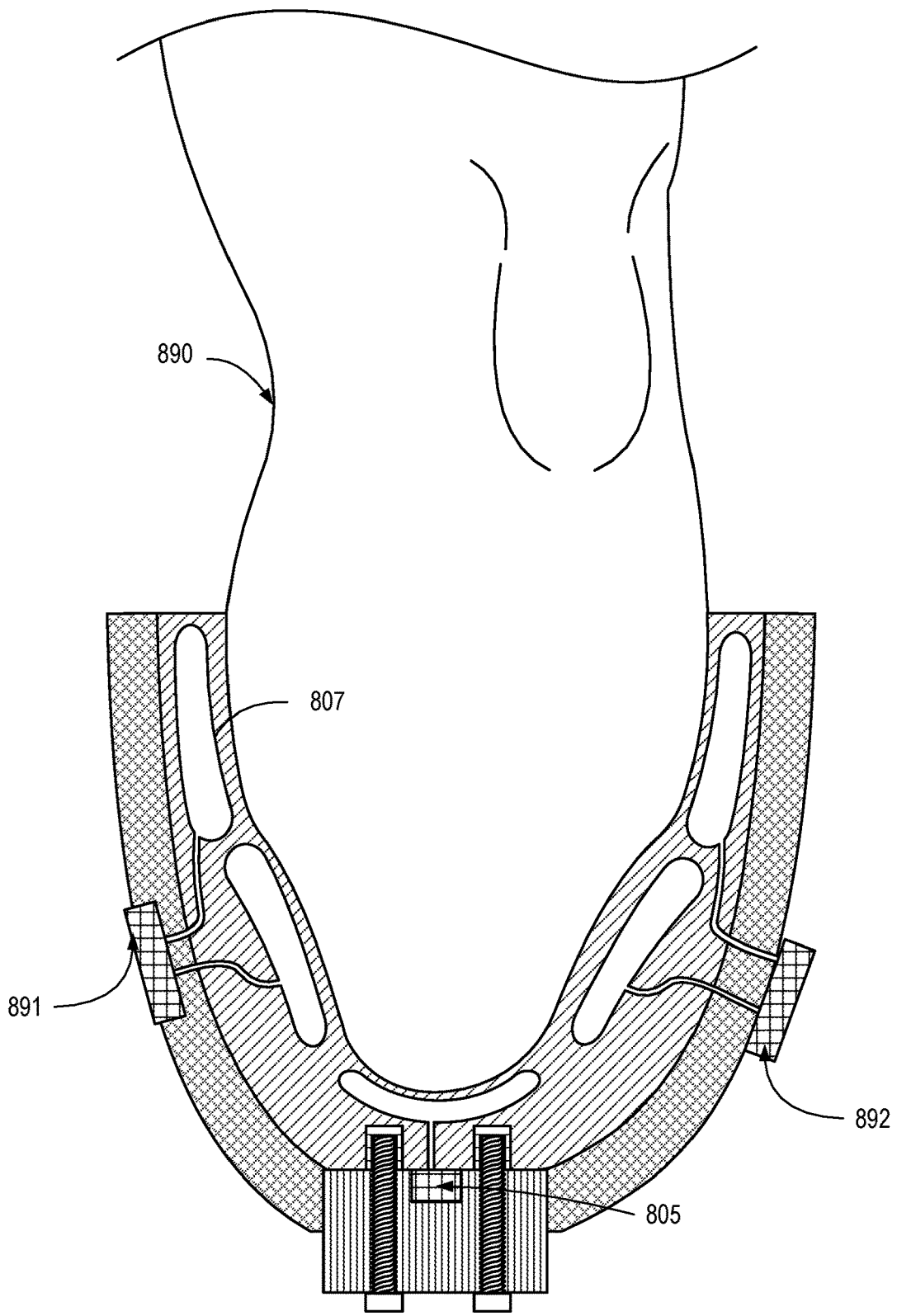
FIG. 8 illustrates a cross-sectional view of an example of a residual limb within the multi-piece prosthetic socket with integrated bladders and reinforced thru-bore attachment features, in which bladder controls are side-mounted, according to one embodiment.

FIG. 8 illustrates a cross-sectional view of an example of a residual limb 890 within the multi-piece prosthetic socket with integrated bladders 807 and reinforced thru-bore attachment features, in which some of the bladder controls 891 and 892 are side-mounted, according to one embodiment. As illustrated, multiple bladder controls 805, 891, and 892 are utilized instead of a single, centralized bladder control.

Figure 9A:
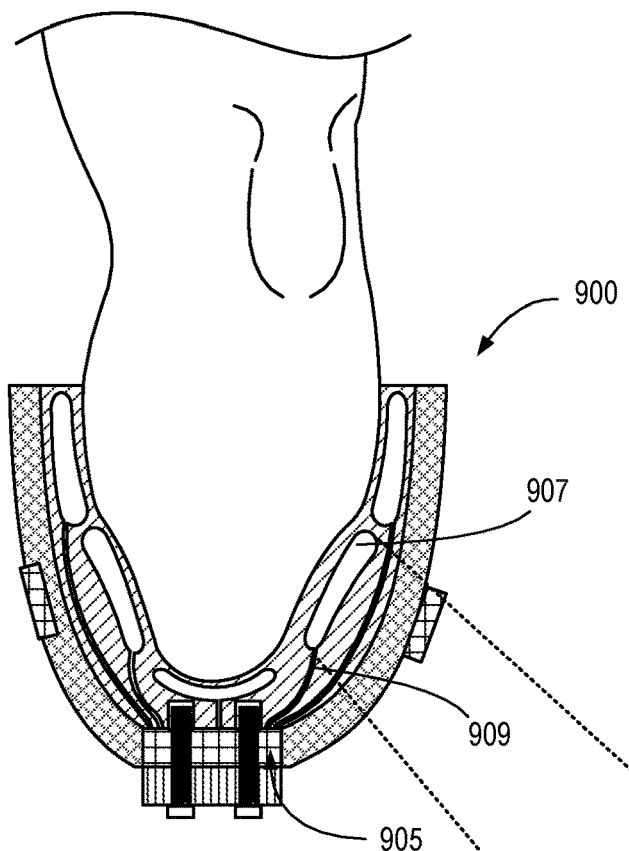
FIGS. 9A and 9B illustrate a multi-piece prosthetic socket in which each integrated bladder comprises a plurality of independently adjustable micro bladders, according to one embodiment.
Figure 9B:
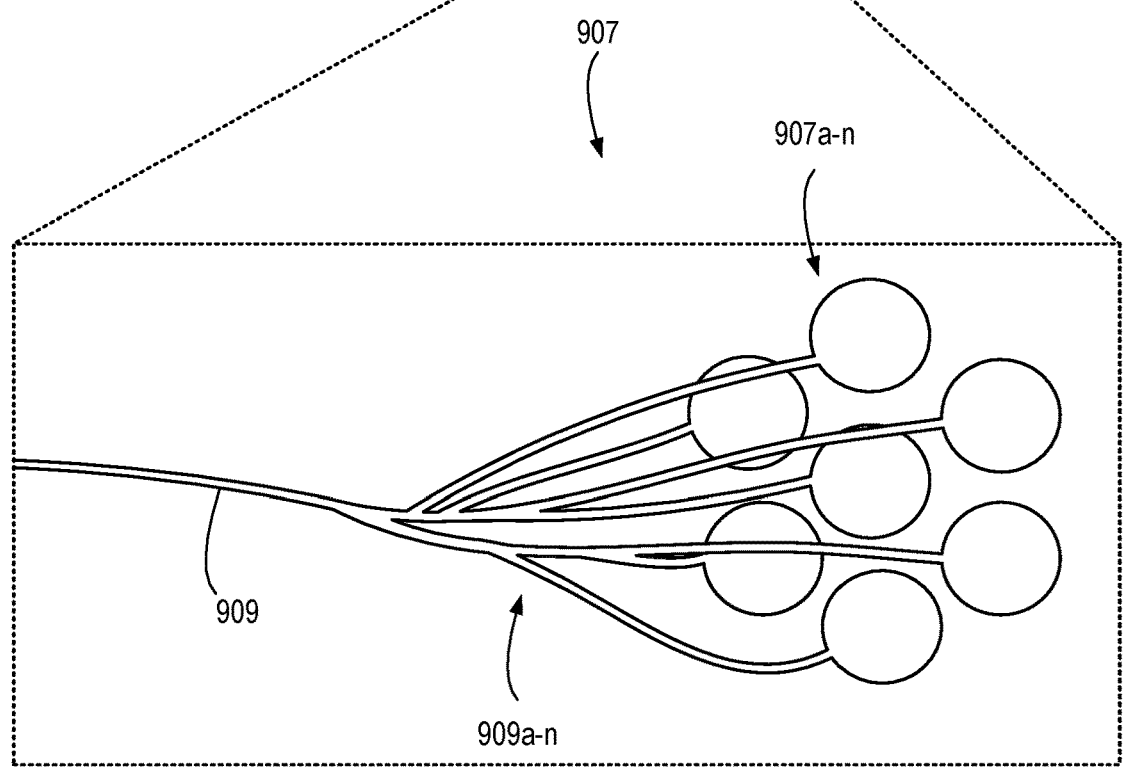

FIGS. 9A and 9B illustrate a multi-piece prosthetic socket 900 in which each integrated bladder 907 comprises a plurality of independently adjustable micro bladders 907a-n, according to one embodiment. The micro bladders 907a-n may be connected via micro tubes 909a-n that join together as a single or bundled tube 909 that connects the micro bladders 907a-n to a centralized pump 905 or plurality of pumps, as described in conjunction with FIG. 8.

In some cases, well-known features, structures, or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations. Thus, all feasible permutations and combinations of embodiments are contemplated.

Several aspects of the embodiments described may be implemented using hardware, firmware, and/or software modules or components. As used herein, a module or component may include various hardware components, firmware code, and/or any type of computer instruction or computer-executable code located within a memory device and/or transmitted as transitory or non-transitory electronic signals over a system bus or wired or wireless network. Many of the embodiments described herein are shown in block diagram form and/or using logic symbols. It is appreciated that various elements of each of the illustrated and described embodiments could be implemented using FPGAs, custom application-specific integrated circuits (ASICs), and/or as hardware/software combinations. The scope of the present disclosure should, therefore, be interpreted to encompass at least the following claims:

What is claimed is:

1. A multi-layer prosthetic socket, comprising:
    a rigid outer shell socket with an asymmetric inner surface contour with curves forming an inner depression to capture an insert socket with corresponding surface features;
    a customized prosthetic insert socket with:
        an asymmetric outer contour with outer curves forming an outer protrusion that corresponds to the inner depression of the asymmetric inner surface contour of the rigid outer shell socket,
        wherein the asymmetric inner surface contour of the rigid outer shell socket operates to capture and secure the customized prosthetic insert socket within the rigid outer shell socket upon insertion of the customized prosthetic insert socket into the rigid outer shell socket, and
        an inner contour that corresponds to a residual limb surface contour of a residual limb of a patient, wherein the inner contour of the customized prosthetic insert socket is adjusted to fit the residual limb surface contour without modifying the asymmetric outer contour of the customized prosthetic insert socket,
        wherein the asymmetric outer contour of the customized prosthetic insert socket is different than the inner contour of the customized prosthetic insert socket, such that the asymmetric outer contour of the customized prosthetic insert socket is non-conformal with the residual limb surface contour.

2. The multi-layer prosthetic socket of claim 1, further comprising:
    an attachment puck integrated within the rigid outer shell socket, the attachment puck including:
        thru-bores to receive fasteners to fasten the rigid outer shell socket to the customized prosthetic insert socket, and
        attachment features for fastening a prosthetic limb to the attachment puck.

3. The multi-layer prosthetic socket of claim 1, wherein the customized prosthetic insert socket further comprises fastener-receiving apertures reinforced with a reinforcement material.

4. The multi-layer prosthetic socket of claim 1, further comprising:
    a plurality of bladders formed within the customized prosthetic insert socket to be selectively filled to apply pressure on the residual limb of the patient and
    a bladder control device to control the selective filling of the plurality of bladders in the customized prosthetic insert socket.

5. The multi-layer prosthetic socket of claim 4, wherein the bladder control device comprises a pump to control the selective filling of the bladders with a fluid.

6. The multi-layer prosthetic socket of claim 1, wherein the rigid outer shell socket comprises at least one of fiberglass and carbon fiber.

7. The multi-layer prosthetic socket of claim 1, wherein the customized prosthetic insert socket is three-dimensionally printed via a three-dimensional printer.

8. The multi-layer prosthetic socket of claim 1, further comprising a perspiration collection subsystem to expel perspiration from the customized prosthetic insert socket.

9. A prosthetic system, comprising:
    a rigid outer shell socket with an asymmetric inner surface contour with curves forming an inner depression to capture an insert socket with corresponding surface features;
    an attachment puck to facilitate fastening of a prosthetic limb to the rigid outer shell socket;
    a customized prosthetic insert socket with:
        an asymmetric outer contour with curves forming an outer protrusion that corresponds to the inner depression of the asymmetric inner surface contour of the rigid outer shell socket, and
        an inner contour that corresponds to a residual limb surface contour of a patient,
        wherein the outer protrusion of the asymmetric outer contour of the customized prosthetic insert socket and the inner depression of the asymmetric inner surface contour of the rigid outer shell socket interact to selectively secure the customized prosthetic insert socket within the rigid outer shell socket,
        wherein the asymmetric outer contour of the customized prosthetic insert socket is different than the inner contour of the customized prosthetic insert socket, such that the asymmetric outer contour of the customized prosthetic insert socket is non-conformal with the residual limb surface contour.

10. The prosthetic system of claim 9, further comprising at least one bladder integrated within the customized prosthetic insert socket between the asymmetric outer contour of the customized prosthetic insert socket and the inner contour of the customized prosthetic insert socket, wherein the asymmetric outer contour of the customized prosthetic insert remains non-conformal with the residual limb when the at least one bladder is filled and when the at least one bladder is emptied.

11. The prosthetic system of claim 10, further comprising a pump integrated within the attachment puck to selectively fill the at least one bladder.

12. The prosthetic system of claim 11, wherein the pump integrated within the attachment puck comprises one of a manually controlled pump and an electronically controlled pump.

13. The prosthetic system of claim 9, wherein the rigid outer shell socket comprises at least one of fiberglass and carbon fiber.

14. The prosthetic system of claim 9, wherein the customized prosthetic insert socket is three-dimensionally printed via a three-dimensional printer.

15. The prosthetic system of claim 9, further comprising a perspiration collection subsystem to expel perspiration from the customized prosthetic insert socket.

16. A method comprising:
    determining a surface contour of a residual limb of a patient;
    selecting a rigid outer shell socket of a particular size from a plurality of premade rigid outer shell sockets of varying sizes, based on the residual limb of the patient, wherein the rigid outer shell socket includes an asymmetric inner surface contour with curves forming an inner depression to capture an insert socket with corresponding surface features;
    printing, via a three-dimensional printer, a prosthetic insert socket with:
        an inner contour that corresponds to the surface contour of the residual limb of the patient,
        an asymmetric outer contour with outer curves forming an outer protrusion that corresponds to the inner depression of the asymmetric inner surface contour of the selected rigid outer shell socket, and
        wherein the asymmetric outer contour of the prosthetic insert socket is different than the inner contour of the prosthetic insert socket, such that the asymmetric outer contour of the prosthetic insert socket is non-conformal with the surface contour of the residual limb;
    inserting the residual limb of the patient within the prosthetic insert socket; and
    inserting the prosthetic insert socket within the rigid outer shell socket to cause the inner depression of the rigid outer shell socket to interact with the outer protrusion of the asymmetric outer contour of the prosthetic insert socket, such that the prosthetic insert socket is captured within the rigid outer shell socket.

17. The method of claim 16, wherein the prosthetic insert socket is printed with a plurality of voids within the prosthetic insert socket between the asymmetric outer contour of the prosthetic insert socket and the inner contour of the prosthetic insert socket with a connection void to form a tube to connect the plurality of voids to a pump.

18. The method of claim 17, further comprising:
    filling the plurality of voids with a pump to adjust a fit between the inner contour of the prosthetic insert socket and the residual limb of the patient without modifying the asymmetric outer contour of the prosthetic insert socket.

19. The method of claim 18, wherein each of the plurality of voids is selectively filled with at least one of a gas and a liquid.

20. The method of claim 17, further comprising:
    connecting a prosthetic limb to an attachment puck integrated within the selected rigid outer shell socket.

* * * * *